US010010696B2

(12) United States Patent
Sprinkle et al.

(10) Patent No.: US 10,010,696 B2
(45) Date of Patent: Jul. 3, 2018

(54) PRODUCT GAS CONCENTRATOR AND METHOD ASSOCIATED THEREWITH

(71) Applicant: Invacare Corporation, Elyria, OH (US)

(72) Inventors: Thomas B. Sprinkle, Rocky River, OH (US); William J. Daniels, Wadsworth, OH (US); Thomas A. Drobnak, Olmsted Township, OH (US); David G. Felty, Parma, OH (US); Valentine A. Hodos, Cleveland, OH (US); Martin J. Fabian, Bay Village, OH (US); Samuel J. Shelnutt, North Ridgeville, OH (US); Jonathon R. Olszewski, Elyria, OH (US)

(73) Assignee: Invacare Corportion, Elyria, OH (US)

( * ) Notice: Subject to any disclaimer, the term of this patent is extended or adjusted under 35 U.S.C. 154(b) by 0 days.

(21) Appl. No.: 15/193,521

(22) Filed: Jun. 27, 2016

(65) Prior Publication Data

US 2016/0375218 A1 Dec. 29, 2016

Related U.S. Application Data

(60) Continuation of application No. 14/202,536, filed on Mar. 10, 2014, now Pat. No. 9,375,674, which is a (Continued)

(51) Int. Cl.
*B01D 53/02* (2006.01)
*A61M 16/20* (2006.01)
(Continued)

(52) U.S. Cl.
CPC ...... *A61M 16/202* (2014.02); *A61M 16/0063* (2014.02); *A61M 16/0677* (2014.02);
(Continued)

(58) Field of Classification Search
CPC .............. A61M 16/0677; A61M 16/10; A61M 16/101; A61M 2016/0027;
(Continued)

(56) References Cited

U.S. PATENT DOCUMENTS 4,127,395 A   11/1978   McKey et al.
4,144,037 A   3/1979   Armond et al.
(Continued)

FOREIGN PATENT DOCUMENTS

CA   2438457    2/2004
CN   87102164   11/1987
(Continued)

OTHER PUBLICATIONS

Third Office Action from Chinese Application No. 200880021148.6 dated May 2, 2013.
(Continued)

*Primary Examiner* — Christopher P Jones
(74) *Attorney, Agent, or Firm* — Calfee, Halter & Griswold LLP

(57) ABSTRACT

Various equipment and methods associated with providing a concentrated product gas are provided. In one embodiment, the equipment includes an input device first and second sieve tanks, a variable restrictor, and a controller. In one embodiment, the method includes: a) selecting a desired output setting for the concentrated product gas from a plurality of output settings, b) separating one or more adsorbable components from a pressurized source gaseous mixture via first and second sieve tanks in alternating and opposing pressurization and purging cycles to form the concentrated product gas, and c) selectively controlling a variable restrictor based at least in part on the desired output setting to selectively provide flow between the first and second sieve tanks such that the flow for at least one output
(Continued)

Figure 1:
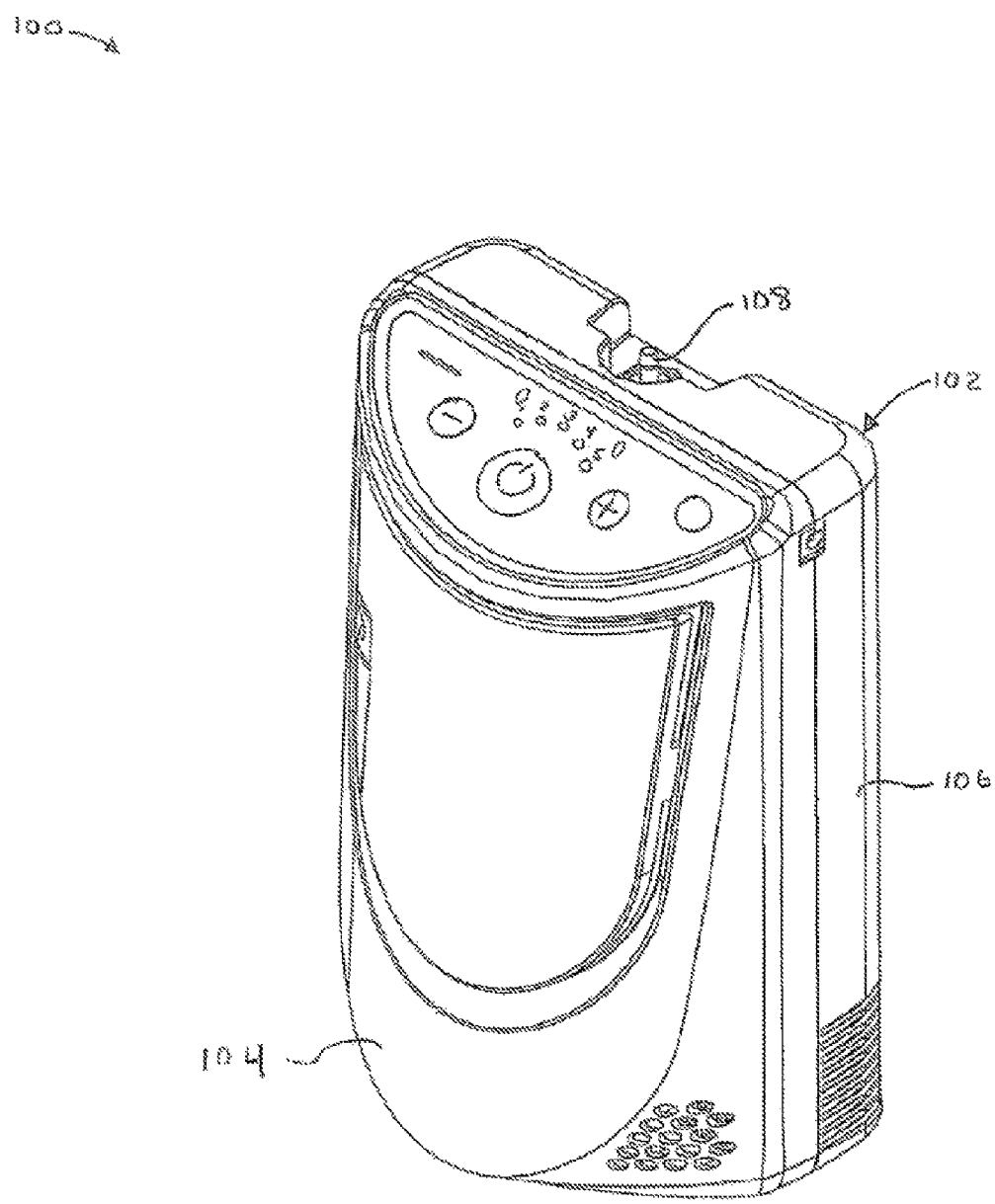

setting is different from the flow for at least one other output setting in relation to corresponding pressurization cycles.

11 Claims, 31 Drawing Sheets

Related U.S. Application Data division of application No. 12/106,861, filed on Apr. 21, 2008, now Pat. No. 8,668,767.

(60) Provisional application No. 60/913,056, filed on Apr. 20, 2007, provisional application No. 60/968,273, filed on Aug. 27, 2007.

(51) Int. Cl.
| | |
|---|---|
| *B01D 53/04* | (2006.01) |
| *B01D 53/053* | (2006.01) |
| *A61M 16/06* | (2006.01) |
| *B01D 53/047* | (2006.01) |
| *A61M 16/10* | (2006.01) |
| *A61M 16/00* | (2006.01) |

(52) U.S. Cl.
CPC ........ *A61M 16/101* (2014.02); *A61M 16/105* (2013.01); *B01D 53/0407* (2013.01); *B01D 53/047* (2013.01); *B01D 53/053* (2013.01); *A61M 16/10* (2013.01); *A61M 16/107* (2014.02); *A61M 2016/003* (2013.01); *A61M 2016/0027* (2013.01); *A61M 2016/0036* (2013.01); *A61M 2205/0216* (2013.01); *A61M 2205/502* (2013.01); *A61M 2205/7536* (2013.01); *A61M 2230/005* (2013.01); *A61M 2230/40* (2013.01); *B01D 2253/108* (2013.01); *B01D 2256/12* (2013.01); *B01D 2257/102* (2013.01); *B01D 2257/502* (2013.01); *B01D 2257/504* (2013.01); *B01D 2257/80* (2013.01); *B01D 2259/402* (2013.01); *B01D 2259/40009* (2013.01); *B01D 2259/40035* (2013.01); *B01D 2259/40043* (2013.01); *B01D 2259/4533* (2013.01); *Y02C 10/08* (2013.01)

(58) Field of Classification Search
CPC ..... A61M 2016/0036; B01D 2253/108; B01D 2256/12; B01D 2257/102; B01D 2257/502; B01D 2257/504; B01D 2259/40009; B01D 2259/40035; B01D 2259/40043; B01D 2259/402; B01D 53/0407; B01D 53/047; B01D 53/053; Y02C 10/08

See application file for complete search history.

(56) References Cited

U.S. PATENT DOCUMENTS

| | | |
|---|---|---|
| 4,247,311 A | 1/1981 | Seibert |
| 4,449,990 A | 5/1984 | Tedford |
| 4,561,287 A | 12/1985 | Rowland |
| 4,575,042 A | 9/1986 | Grimland |
| 4,648,888 A | 3/1987 | Rowland |
| 4,826,510 A | 5/1989 | McCombs |
| 4,832,711 A | 5/1989 | Christel, Jr. et al. |
| 4,932,402 A | 6/1990 | Snook et al. |
| 4,971,609 A | 11/1990 | Pawlos |
| 5,099,837 A | 3/1992 | Russel et al. |
| 5,258,056 A | 11/1993 | Shirley et al. |
| 5,474,595 A | 12/1995 | McCombs |
| 5,593,478 A | 1/1997 | Hill et al. |
| 5,626,131 A | 5/1997 | Chua et al. |
| 5,720,276 A | 2/1998 | Kobatake et al. |
| 5,785,681 A | 7/1998 | Indravudh |
| 5,906,672 A | 5/1999 | Michaels et al. |
| 5,917,135 A | 6/1999 | Michaels et al. |
| 5,988,165 A | 11/1999 | Richey, II et al. |
| 6,051,051 A | 4/2000 | Hees et al. |
| 6,106,245 A | 8/2000 | Cabuz |
| 6,427,690 B1 | 8/2002 | McCombs et al. |
| 6,517,610 B1 | 2/2003 | De La Houssaye |
| 6,520,176 B1 | 2/2003 | Dubois et al. |
| 6,561,187 B2 | 5/2003 | Schmidt et al. |
| 6,629,525 B2 | 10/2003 | Hill et al. |
| 6,651,658 B1 | 11/2003 | Hill et al. |
| 6,691,702 B2 | 2/2004 | Appel et al. |
| 6,764,534 B2 | 7/2004 | McCombs et al. |
| 6,837,244 B2 | 1/2005 | Yagi et al. |
| 6,878,186 B2 | 4/2005 | Neary |
| 6,949,133 B2 | 9/2005 | McCombs et al. |
| 6,962,654 B2 | 11/2005 | Arnaud |
| 7,294,170 B2 | 11/2007 | Richey, II et al. |
| 7,306,657 B2 | 12/2007 | Yagi et al. |
| 7,329,304 B2 | 2/2008 | Bliss et al. |
| 7,393,382 B2 | 7/2008 | Givens |
| 7,445,663 B1 | 11/2008 | Hunter et al. |
| 7,455,717 B2 | 11/2008 | Sprinkle |
| 7,604,005 B2 | 10/2009 | Jagger et al. |
| 7,686,870 B1 | 3/2010 | Deane et al. |
| 7,722,700 B2 | 5/2010 | Sprinkle |
| 7,766,010 B2 | 8/2010 | Jagger et al. |
| 7,875,105 B2 | 1/2011 | Chambers et al. |
| 8,062,003 B2 | 11/2011 | Goertzen et al. |
| 8,070,853 B2 | 12/2011 | Sprinkle |
| 8,262,771 B2 | 9/2012 | Seki et al. |
| 2002/0053286 A1 | 5/2002 | Czabala |
| 2003/0180164 A1 | 9/2003 | Bunner et al. |
| 2003/0215342 A1 | 11/2003 | Higashino |
| 2003/0231967 A1 | 12/2003 | Najafi et al. |
| 2004/0079359 A1 | 4/2004 | Aylsworth et al. |
| 2006/0005842 A1* | 1/2006 | Rashad .............. A61M 16/0666 128/207.18 |
| 2006/0086251 A1 | 4/2006 | Sprinkle |
| 2006/0174872 A1 | 8/2006 | Jagger |
| 2006/0219245 A1 | 10/2006 | Holder |
| 2006/0230929 A1 | 10/2006 | Bliss et al. |
| 2008/0066616 A1 | 3/2008 | Sprinkle |
| 2008/0257145 A1 | 10/2008 | Sprinkle |
| 2009/0065526 A1 | 3/2009 | Sprinkle |
| 2009/0211448 A1 | 8/2009 | McClain |
| 2010/0071698 A1 | 3/2010 | Kiritake |
| 2010/0095841 A1 | 4/2010 | Naheiri |
| 2010/0114218 A1 | 5/2010 | Heath |
| 2010/0242734 A1 | 9/2010 | Maeda et al. |
| 2011/0017216 A1 | 1/2011 | Van Brunt et al. |
| 2011/0315140 A1 | 12/2011 | Shuman |
| 2013/0233168 A1 | 9/2013 | Richey, II |

FOREIGN PATENT DOCUMENTS

| | | |
|---|---|---|
| CN | 1697681 | 11/2005 |
| CN | 1697682 | 11/2005 |
| CN | 101687134 A | 3/2010 |
| DE | 29605889 | 6/1996 |
| DE | 102007 021564 | 11/2008 |
| EP | 420620 | 4/1991 |
| EP | 1661596 | 5/2006 |
| GB | 1270296 | 4/1972 |
| WO | 98/56488 | 12/1998 |
| WO | 98/57165 | 12/1998 |
| WO | 06/92635 A1 | 9/2006 |
| WO | 08/036159 | 3/2008 |
| WO | 08/131338 | 10/2008 |
| WO | 13/134645 | 9/2013 |

OTHER PUBLICATIONS

Response from Chinese Application No. 200880021148.6 dated Jul. 17, 2013.

(56) References Cited

OTHER PUBLICATIONS

First Office Action from Chinese Application No. 201310563818.X dated Feb. 28, 2015.
Search Report from Chinese Application No. 201310563818.X dated Feb. 10, 2015.
First Office Action in Colombian Application No. 09028163 dated Aug. 22, 2012.
Response from Colombian Application No. 09028163 dated Nov. 6, 2012.
Partial International Search Report from PCT/US13/46086 dated Sep. 23, 2013.
International Search Report from PCT/US13146086 dated Dec. 12, 2013.
International Preliminary Report on Patentability from PCT/US13/046086 dated Dec. 23, 2014.
International Search Report and Written Opinion from PCT/US14/10409 dated Jun. 12, 2014.
First Office Action from Chinese Application No. 201380024109.2 dated Aug. 7, 2015.
Search Report from European Application No. 15170789.0 dated Dec. 2, 2015.
Notice of Allowance from U.S. Appl. No. 14/202,536 dated Mar. 3, 2016.
Rule 69 EPC Communication from European Application No. 15170789.0 dated Feb. 1, 2016.
Response to Office Action from Canadian Application No. 2,871,228 dated May 3, 2015.
Office Action from Canadian Application No. 2,871,228 dated May 11, 2016.
Communication pursuant to Article 94(3) EPC from European Application No. 13710764.5 dated Apr. 13, 2016.
Response to Office Action from Chinese Application No. 201380024109.2 dated Feb. 22, 2016.
Office Action from Chinese Application No. 201380024109.2 dated Jun. 13, 2016.
First Examination Report from Australian Application No. 2013229908 dated Mar. 24, 2017.
Communication Pursuant to Article 94(3) EPC from European Application No. 14703185.0 dated Feb. 22, 2017.
Second Office Action from Chinese Application No. 201480013306.9 dated Mar. 8, 2017.
First Examination Report from New Zealand Application No. 709919 dated Feb. 3, 2017.
Office Action from U.S. Appl. No. 14/852,721 dated Oct. 18, 2016.
Office Action from Canadian Application No. 2,871,228 dated Nov. 28, 2016.
First Office Action from Chinese Application No. 201480013306.9 dated Jul. 13, 2016.
First Examination report from New Zealand Application No. 722551 dated Aug. 4, 2016.
International Search Report and Written Opinion from PCT/US07/18468 dated Feb. 11, 2008.
International Search Report and Written Opinion from PCT/US08/61022 dated Jul. 18, 2008.
International Search Report and Written Opinion from PCT/US13/029885 dated May 31, 2013.
Invacare Corporation, Oxygen Products Brochure, Form No. 05-054, 20 pages, copyright 2005.
Invacare Corporation, Oxygen Products Brochure, Form. No. 05-054, 16 pgs., copyright 2008.
Invacare Corp., XP02 Portable Concentrator, Invacare Product Catalog, www.invacare.com/cgi-bin/imhqprd/inv_catalog/prod_cat_detail.jsp?s=0 & prodID=XPO100 & catOID-536885301, printed Mar. 17, 2008, 1 pg.
Office action from U.S. Appl. No. 11/258,480 dated Feb. 12, 2008.
Response to Office action from U.S. Appl. No. 11/258,480 dated May 9, 2008.
Notice of Allowance from U.S. Appl. No. 11/258,480 dated Jul. 21, 2008.
Office action from U.S. Appl. No. 11/522,683 dated Jun. 8, 2009.
Response to Office action from U.S. Appl. No. 11/522,683 dated Dec. 8, 2009.
Notice of Allowance from U.S. Appl. No. 11/522,683 dated Dec. 30, 2009.
Office action from U.S. Appl. No. 12/106,861 dated Jul. 21, 2010.
Response from U.S. Appl. No. 12/106,861 dated Oct. 21, 2010.
Office action from U.S. Appl. No. 12/106,861 dated Dec. 7, 2010.
Response from U.S. Appl. No. 12/106,861 dated Apr. 6, 2011.
Office Action from U.S. Appl. No. 12/106,861 dated Jun. 14, 2012.
Amendment from U.S. Appl. No. 12/106,861 dated Oct. 15, 2012.
Final Office Action from U.S. Appl. No. 12/106,861 dated Oct. 23, 2012.
Amendment with RCE from U.S. Appl. No. 12/106,861 dated Jan. 23, 2013.
Notice of Allowance for U.S. Appl. No. 12/106,861 dated Jun. 12, 2013.
Response to Office Action from Canadian Application No. 2,663,902 dated Apr. 20, 2011.
Office action from U.S. Appl. No. 12/274,026 dated Nov. 8, 2010.
Amendment with Terminal Disclaimer from U.S. Appl. No. 12/274,026 dated Mar. 8, 2011.
Notice of Allowance from U.S. Appl. No. 12/274,026 dated May 11, 2011.
Notice of Allowance from U.S. Appl. No. 12/274,026 dated Sep. 28, 2011.
Office Action from U.S. Appl. No. 13/790,826 dated Sep. 9, 2014.
Response to Office Action from U.S. Appl. No. 13/790,826 dated Dec. 9, 2014.
Notice of Allowance from U.S. Appl. No. 13/790,826 dated Jan. 22, 2015.
Notice of Allowance from U.S. Appl. No. 13/790,826 dated May 11, 2015.
Office Action from US. U.S. Appl. No. 13/839,954 dated Oct. 9, 2014.
Response to Office Action from U.S. Appl. No. 13/839,954 dated Nov. 9, 2014.
Notice of Allowance from U.S. Appl. No. 13/839,954 dated Feb. 20, 2015.
Office Action from U.S. Appl. No. 13/790,473 dated Sep. 9, 2014.
Response to Office Action from U.S. Appl. No. 13/790,473 dated Dec. 9, 2014.
Office Action from U.S. Appl. No. 13/790,312 dated Mar. 5, 2015.
Office action from Canadian Application No. 2,663,902 dated Oct. 20, 2010.
Response to Office Action from U.S. Appl. No. 13/790,312 dated Aug. 4, 2015.
Notice of Allowance from U.S. Appl. No. 13/790,312 dated Aug. 20, 2015.
Notice of Allowance from U.S. Appl. No. 13/790,473 dated Jan. 12, 2015.
Notice of Allowance from U.S. Appl. No. 13/790,473 dated Apr. 21, 2015.
Examination Report from AU Application No. 2007297814 dated Feb. 4, 2010.
Response from Australian Application No. 2007297814 dated Apr. 4, 2011.
Office action from Australian Application No. 2008242596 dated Jul. 14, 2010.
Response from Australian Application No. 2008242596 dated Sep. 26, 2011.
Further Examination Report from Australian Application No. 2008242596 dated Oct. 7, 2011.
Response to Examiner's Second Report from Australian Application No. 2008242596 dated Feb. 8, 2012.
First Office Action in AU Patent Application No. 2012203342 dated Dec. 21, 2012.
First Examination Report from Australian Application No. 2014203773 dated Aug. 7, 2015.
Office Action from Canadian Application No. 2,871,228 dated Nov. 9, 2015.
Response to Office Action from U.S. Appl. No. 14/852,721 dated Jan. 18, 2017.

(56) References Cited

OTHER PUBLICATIONS

Notice of Allowance from U.S. Appl. No. 14/852,721 dated Mar. 1, 2017.
Communication Pursuant to Article 94(3) EPC from European Application No. 13710764.5 dated Jan. 3, 2017.
Office action from Canadian Application No. 2,684,871 dated May 31, 2011.
Response to Office Action from Canadian Application No. 2,684,871 dated Nov. 30, 2011
First Office Action in Canadian Application No. 2,793,228 dated Jan. 8, 2013.
Response from Canadian Application No. 2,793,228 dated Jun. 17, 2013.
Second Office Action from Canadian Application No. 2,793,228 dated Jul. 29, 2013.
Response to Office Action from Canadian Application No. 2,793,228 dated Jan. 29, 2014.
Communication from EP Application No. 07837126.7 dated Sep. 3, 2010.
Response from EP Application No. 07837126.7 dated Mar. 14, 2011.
Exam Report from EP Application No. 07837126.7 dated Sep. 27, 2011.
Response from EP Application No. 07837126.7 dated Mar. 16, 2012.
Notice of Grant of EP Application No. 07837126.7 dated Jul. 8, 2013.
Search Report from EP Application No. 08746446.7 dated Aug. 2, 2011.
Response from EP Application No. 08746446.7 dated Feb. 3, 2012.
Office Action from EP Application No. 08746446.7 dated Jun. 27, 2012.
Response to Communication from EP Application No. 08746446.7 dated Dec. 27, 2012.
Response to OA requesting claims in EP Application No. 12184137.3 dated Dec. 4, 2012.
Extended EP Search Report for EP Application No. 12184137.3 dated Feb. 14, 2013.
Response from European Application No. 12184137.3 dated Aug. 27, 2013.
Office action from European Application No. 12184137.3 dated Oct. 1, 2013.
Response from European Application No. 12184137.3 dated Apr. 11, 2014.
Communication to Rules 161(1) and 162 EPC from European Application No. 137107464.5 dated Nov. 7, 2014.
Summons to Attend Oral Hearing from European Application No. 12184137.3 dated Apr. 8, 2015.
Examination Report from New Zealand Application No. 575,059 dated Dec. 15, 2010.
Response to New Zealand Application No. 575,059 dated May 8, 2012.
Office Action from New Zealand Application No. 575,059 dated May 22, 2012.
Response to Office Action from New Zealand Application No. 575,059 dated Jun. 28, 2012.
First Examination Report from New Zealand Application No. 580,515 dated Mar. 23, 2011.
Examination Report from New Zealand Application No. 580,515 dated Aug. 14, 2012.
Response to First Examination Report from New Zealand Application No. 580,515 dated Jul. 23, 2012.
Response to Second Examination Report from New Zealand Application No. 580,515 dated Oct. 18, 2012.
Third Examination Report from New Zealand Application No. 580,515 dated Nov. 9, 2012.
Response to Third Examination Report from New Zealand Application No. 580,515 dated Nov. 15, 2012.
Office action from New Zealand Application No. 603120 dated Oct. 26, 2012.
Response from New Zealand Application No. 603120 dated Dec. 23, 2013.
First Examination Report from New Zealand Application No. 619,142 dated Jan. 29, 2014.
Examination Report from New Zealand Application No. 619,142 dated May 6, 2015.
First Examination Report from New Zealand Application No. 631,712 dated Apr. 28, 2015.
First Examination Report from New Zealand Application No. 706,769 dated May 6, 2015.
Office Action from Chinese Application No. 200780034658.2 dated Nov. 14, 2011.
Response to Office Action from Chinese Application No. 200780034658.2 dated May 4, 2012.
Office action from Chinese Application No. 200780034658.2 dated Aug. 1, 2012.
Response to Second Office action from Chinese Application No. 200780034658.2 dated Dec. 17, 2012.
Third Office Action from Chinese Application No. 200780034658.2 dated Jan. 21, 2013.
Response to Third Office Action from Chinese Application No. 200780034658.2 dated Jun. 5, 2013.
Office action from Chinese Application No. 200780034658.2 dated Jun. 19, 2013.
Response from Chinese Application No. 200780034658.2 dated Nov. 4, 2011.
Office Action from Chinese Application No. 200880021148.6 dated Nov. 1, 2014.
Response to Office Action from Chinese Application No. 200880021148.6 dated May 13, 2012.
Second Office Action from Chinese Application No. 200880021148.6 dated Oct. 25, 2012.
Response from Chinese Application No. 200880021148.6 dated Mar. 8, 2013.

\* cited by examiner

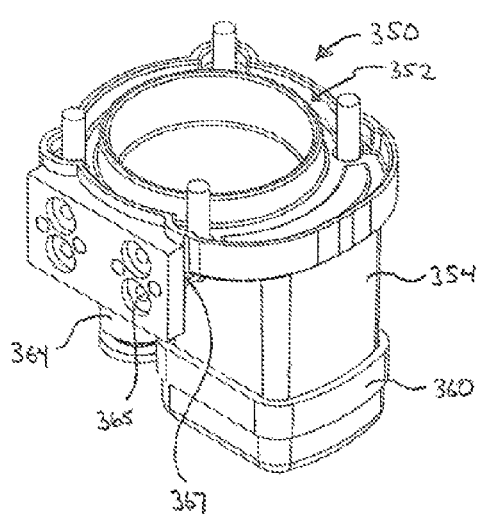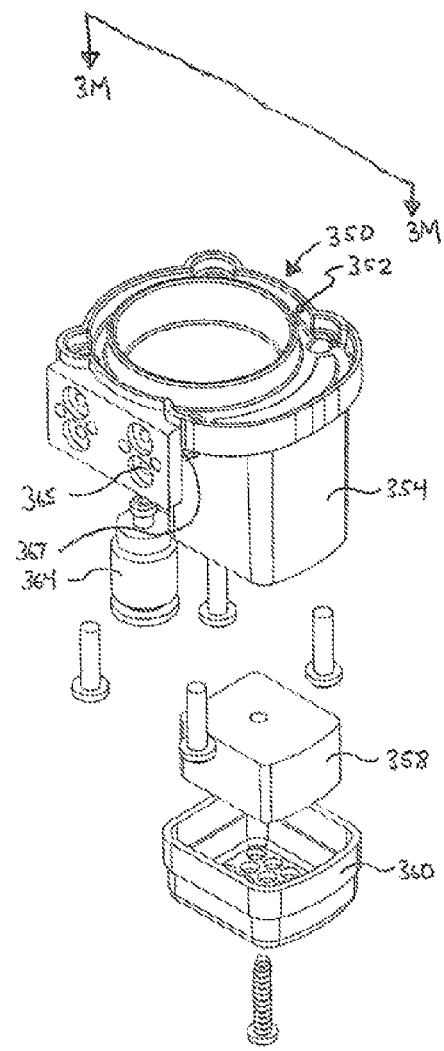
FIG. 3K                    FIG. 3L

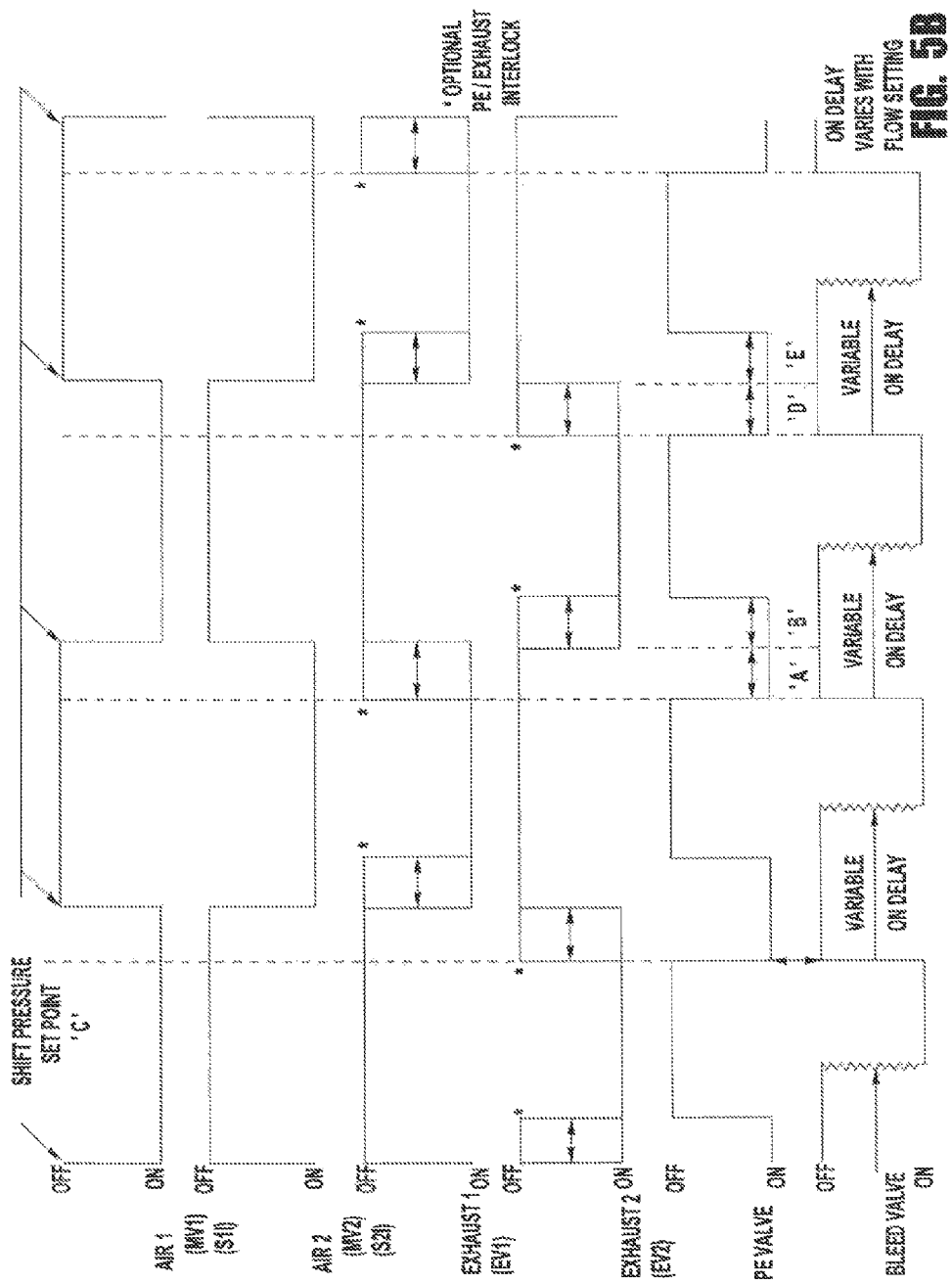

PRODUCT GAS CONCENTRATOR AND METHOD ASSOCIATED THEREWITH

CROSS-REFERENCE TO RELATED APPLICATIONS

This application is a continuation of U.S. Utility patent application Ser. No. 14/202,536, filed on Mar. 10, 2014, which is a divisional of U.S. Utility patent application Ser. No. 12/106,861, filed Apr. 21, 2008, now U.S. Pat. No. 8,668,767, which issued Mar. 11, 2014, which claims priority to U.S. Provisional Patent Application Nos. 60/913,056, filed Apr. 20, 2007, and 60/968,273, filed Aug. 27, 2007. This application is related to co-pending U.S. Utility patent application Ser. No. 11/258,480, filed Oct. 25, 2005 and Ser. No. 11/522,683, filed Sep. 18, 2006. This application is also related to co-pending International Patent Application Numbers PCT/US07/18468, filed Sep. 18, 2006 and PCT/US08/61022, filed Apr. 21, 2008. The contents of all above-identified patent application(s) and patent(s) are fully incorporated herein by reference.

BACKGROUND

Various applications exist for the separation of gaseous mixtures. For example, the separation of nitrogen from atmospheric air can provide a highly concentrated source of oxygen. These various applications include the provision of elevated concentrations of oxygen for medical patients and flight personnel. Hence, it is desirable to provide systems that separate gaseous mixtures to provide a concentrated product gas, such as a breathing gas with a concentration of oxygen.

Several existing product gas or oxygen concentrators, for example, are disclosed in U.S. Pat. Nos. 4,449,990, 5,906,672, 5,917,135, and 5,988,165 which are commonly assigned to Invacare Corporation of Elyria, Ohio and fully incorporated herein by reference.

SUMMARY

In one aspect, an apparatus associated with providing a concentrated product gas is provided. In one embodiment, the apparatus includes an input device adapted to select a desired output setting for the concentrated product gas from a plurality of output settings, first and second sieve tanks arranged to separate one or more adsorbable components from a pressurized source gaseous mixture in alternating and opposing pressurization and purging cycles to form the concentrated product gas, a variable restrictor to selectively provide an adjustable flow between the first and second sieve tanks, and a controller in operative communication with the input device and variable restrictor to selectively control the variable restrictor based at least in part on the desired output setting such that the flow between the first and second sieve tanks for at least one output setting is different from the flow between the first and second sieve tanks for at least one other output setting in relation to corresponding pressurization cycles.

In another embodiment, the apparatus includes first and second sieve tanks arranged to separate one or more adsorbable components from a pressurized source gaseous mixture in alternating and opposing pressurization and purging cycles to form the concentrated product gas and a controller in operative communication with the first and second sieve tanks to selectively control the pressurization and purging cycles over a plurality of predetermined altitude ranges while maintaining an acceptable purity level for the concentrated product gas.

In still another embodiment, the apparatus includes an input device to select a first desired output setting for the concentrated product gas, a product gas source to provide the concentrated product gas for dispensing, a pressure sensor monitoring a pressure of the concentrated product gas, a conserver valve including an output connection associated with a user, a vent connection associated with a vent port, and a gas connection associated with the concentrated product gas, wherein the output connection is switched from the vent connection to the gas connection and vice versa, and a controller in operative communication with the input device and pressure sensor to selectively switch the conserver valve to selectively dispense the concentrated product gas based at least in part on the selected output setting and monitored pressure.

In yet another embodiment, the apparatus includes a body forming an assembly with a sieve bed portion and a product tank portion separated by a common wall, the sieve bed portion adapted to separate one or more adsorbable components from a pressurized source gaseous mixture, the product tank portion adapted to store a volume of concentrated product gas.

In still yet another embodiment, the apparatus includes a frame comprising a plurality of structural support members forming a cage-like structure and a compressor suspended within the frame by a plurality of suspension members and adapted to provide a pressurized source gaseous mixture to first and second sieve tanks of a product gas concentrator.

In another embodiment, the apparatus includes a main body enclosing a filter, the filter adapted to filter a concentrated product gas from a product gas source and provide filtered product gas.

In another aspect, a method associated with providing a concentrated product gas is provided. In one embodiment, the method includes: a) selecting a desired output setting for the concentrated product gas from a plurality of output settings, b) separating one or more adsorbable components from a pressurized source gaseous mixture via first and second sieve tanks in alternating and opposing pressurization and purging cycles to form the concentrated product gas, and c) selectively controlling a variable restrictor based at least in part on the desired output setting to selectively provide flow between the first and second sieve tanks such that the flow between the first and second sieve tanks for at least one output setting is different from the flow between the first and second sieve tanks for at least one other output setting in relation to corresponding pressurization cycles.

In another embodiment, the method includes: a) separating one or more adsorbable components from a pressurized source gaseous mixture via first and second sieve tanks in alternating and opposing pressurization and purging cycles to form the concentrated product gas and b) selectively controlling the pressurization and purging cycles over a plurality of predetermined altitude ranges while maintaining an acceptable purity level for the concentrated product gas.

In still another embodiment, the method includes: a) selecting a first desired output setting for the concentrated product gas, b) providing a product gas source for supplying the concentrated product gas to be dispensed, c) monitoring a pressure of the concentrated product gas, and d) selectively switching an output connection associated with a user from a vent connection associated with a vent port to a gas connection associated with the concentrated product gas and vice versa to selectively dispense the concentrated product gas based at least in part on the selected output setting and monitored pressure.

DRAWINGS

These and other features, aspects, and advantages of the present invention will become better understood with regard to the accompanying drawings, following description, and appended claims.

Figure 2:
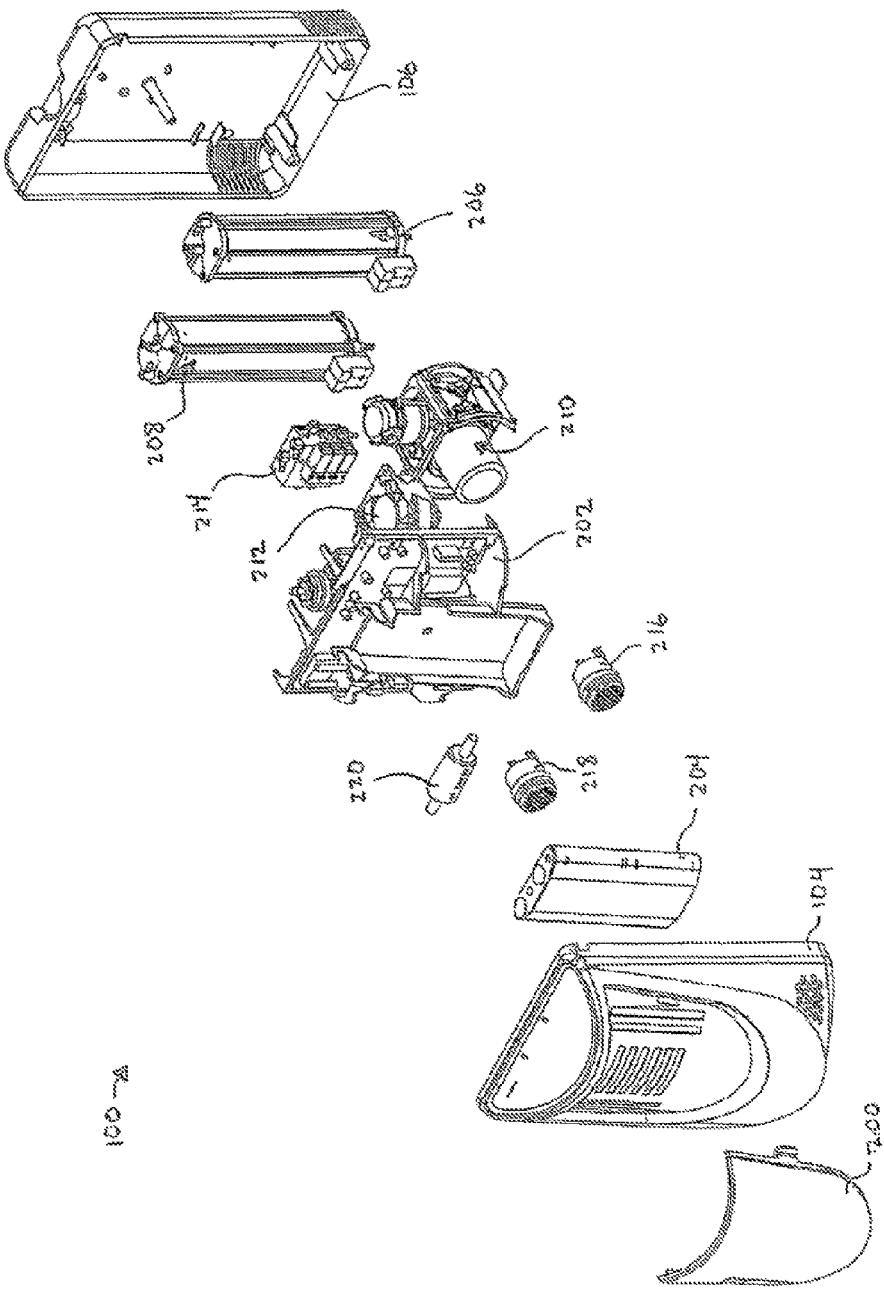
Figure 3A:
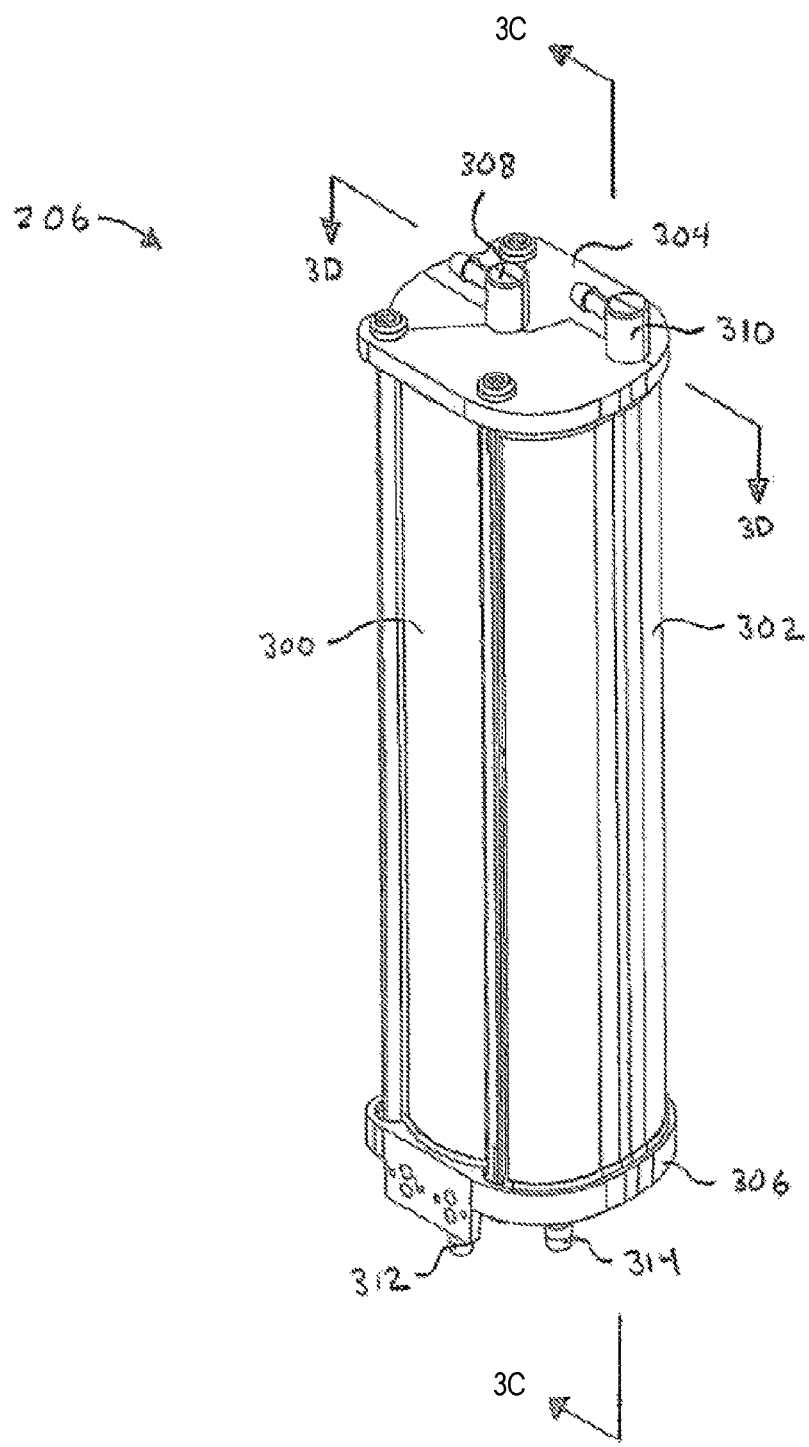
Figure 4A:
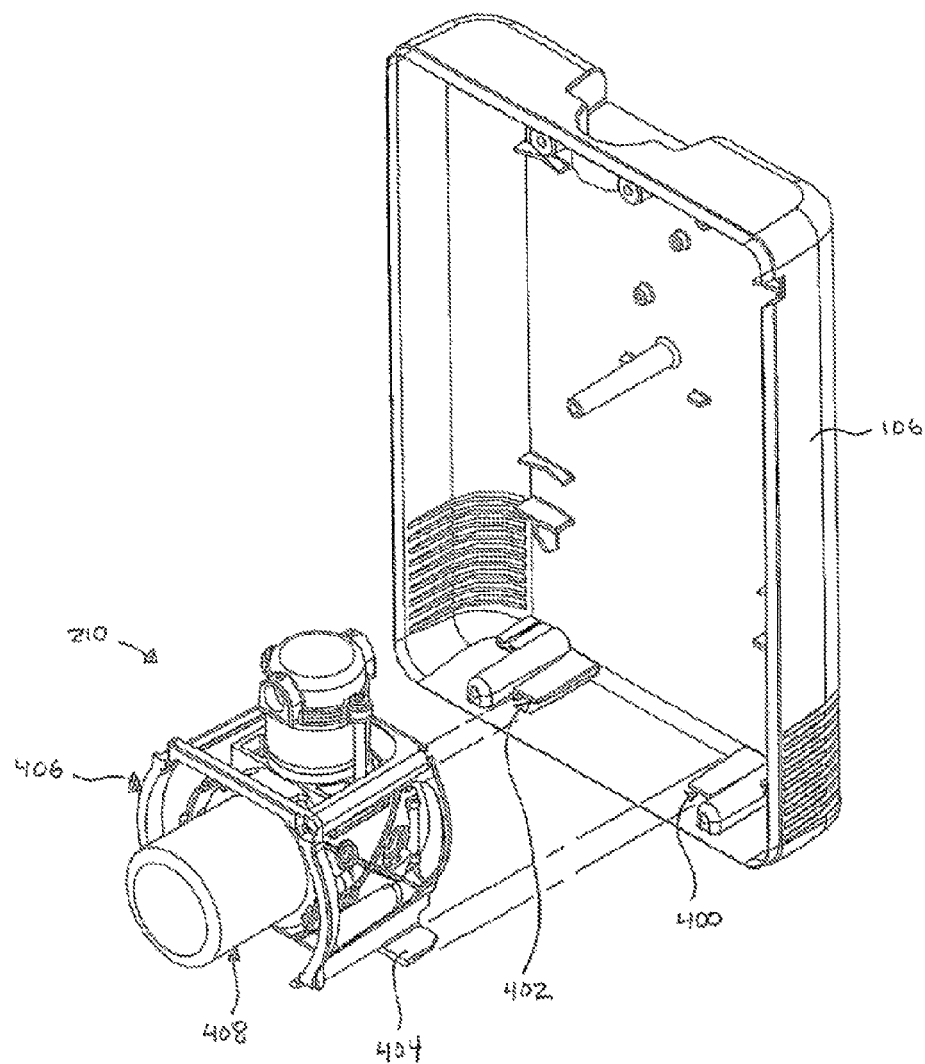
Figure 4B:
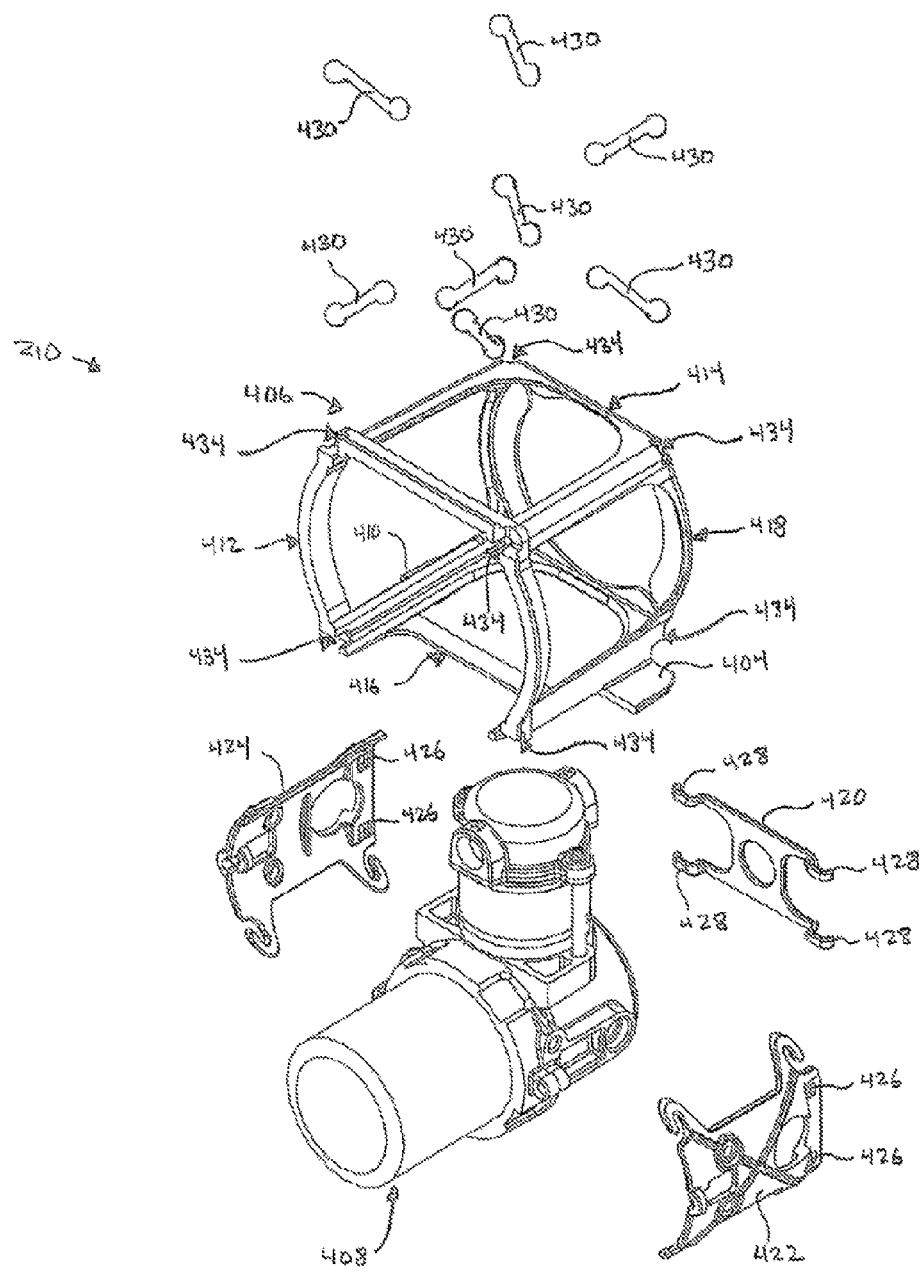
Figure 4C:
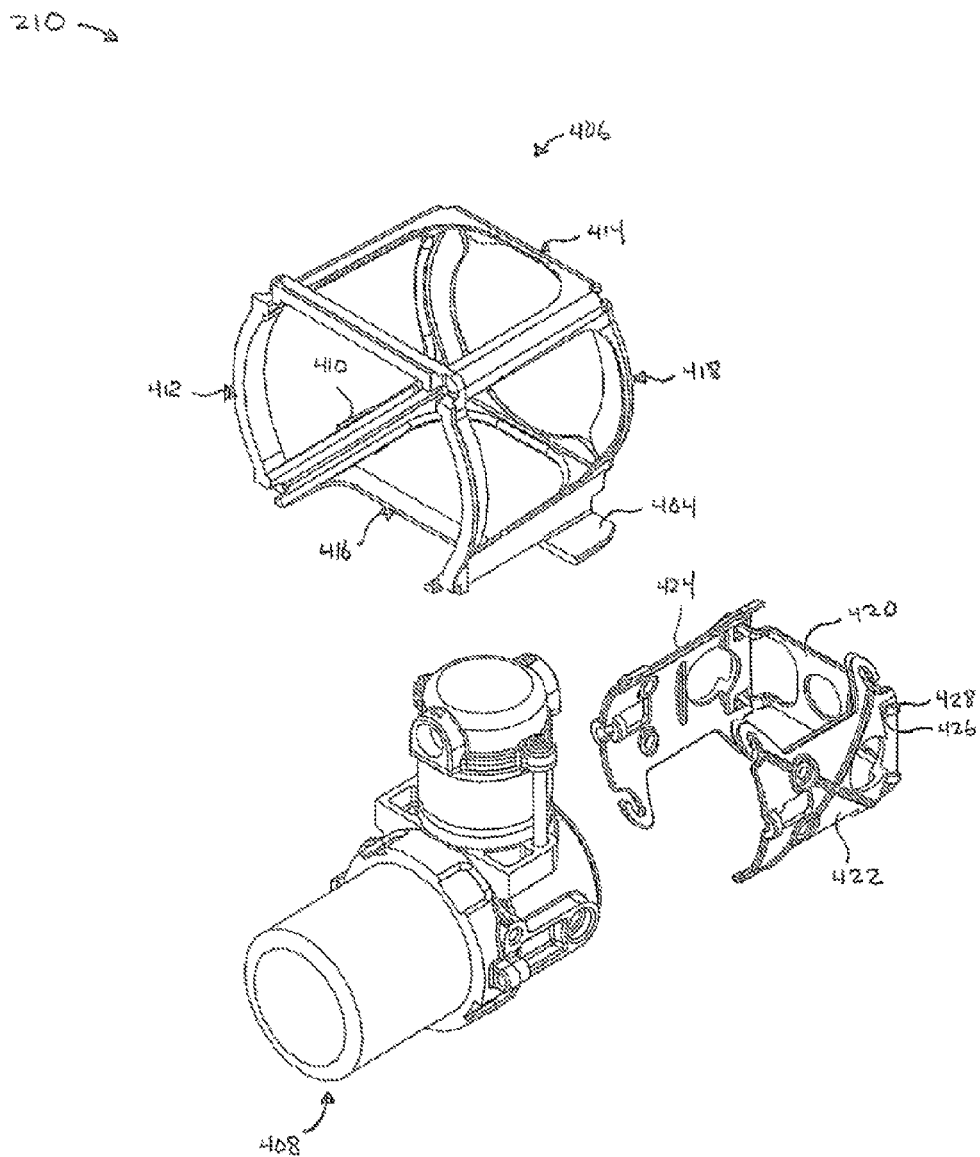
Figure 4D:
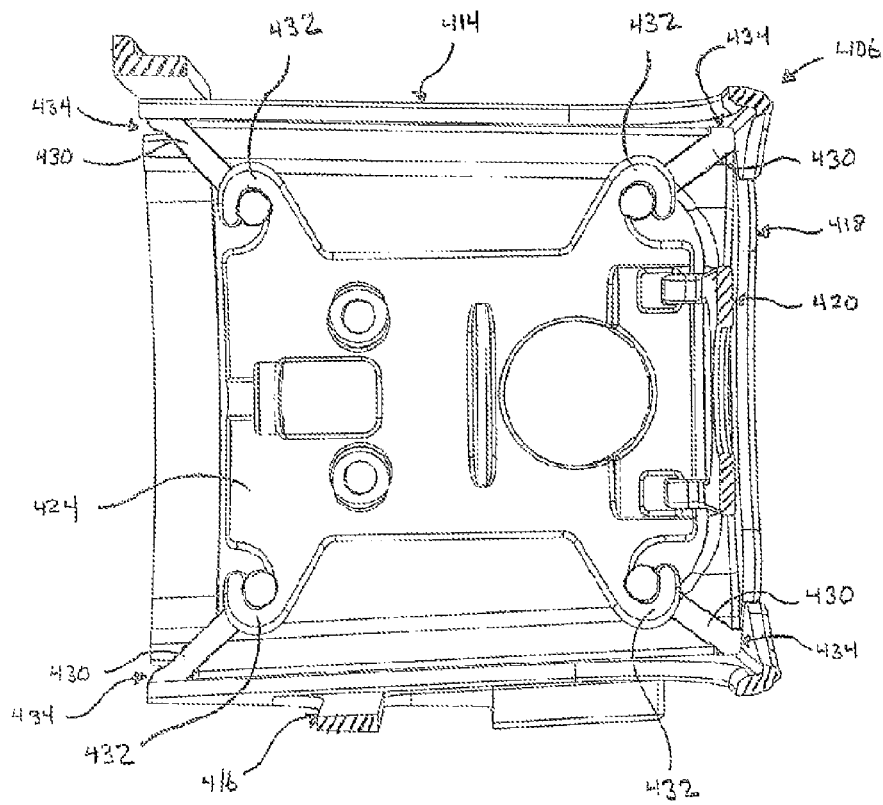
Figure 4E:
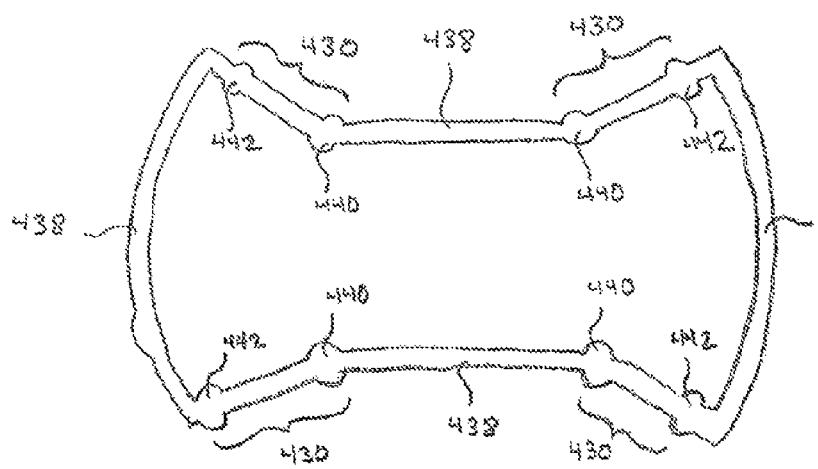
Figure 4F:
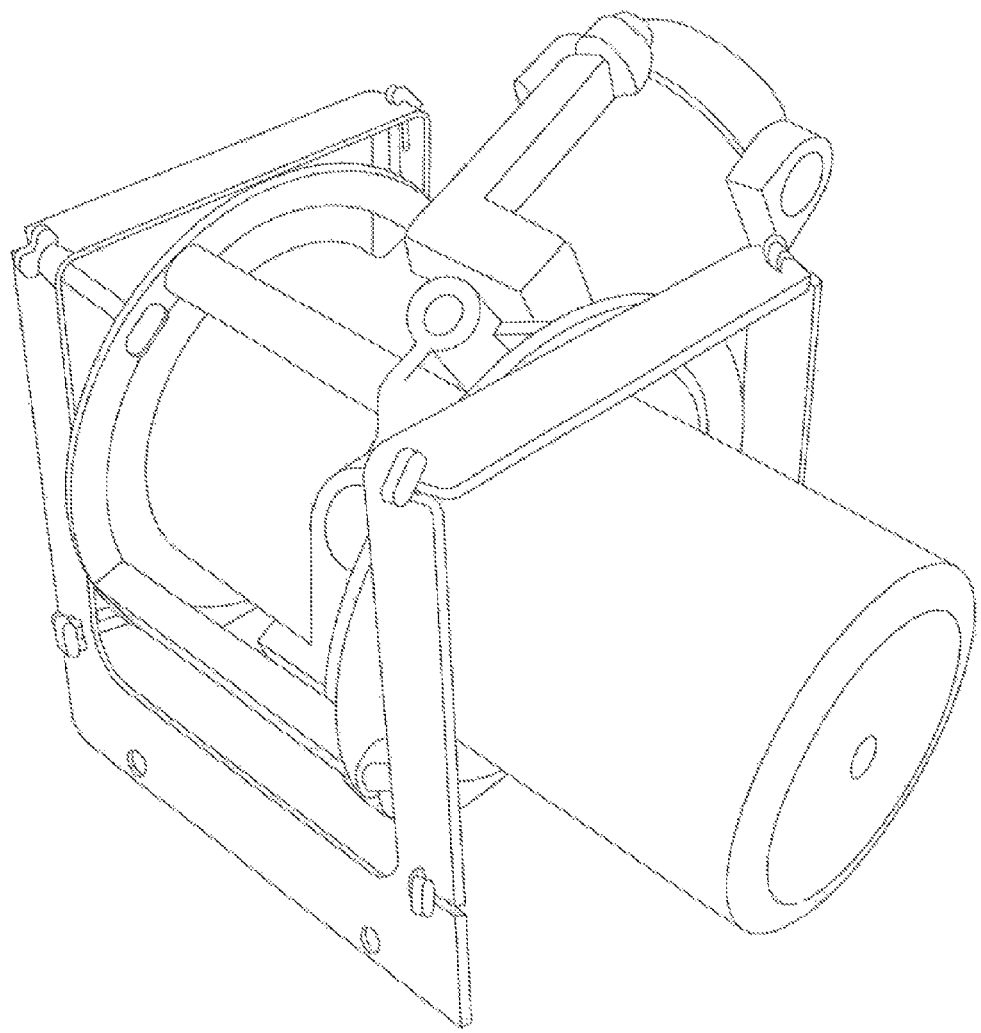
Figure 5A:
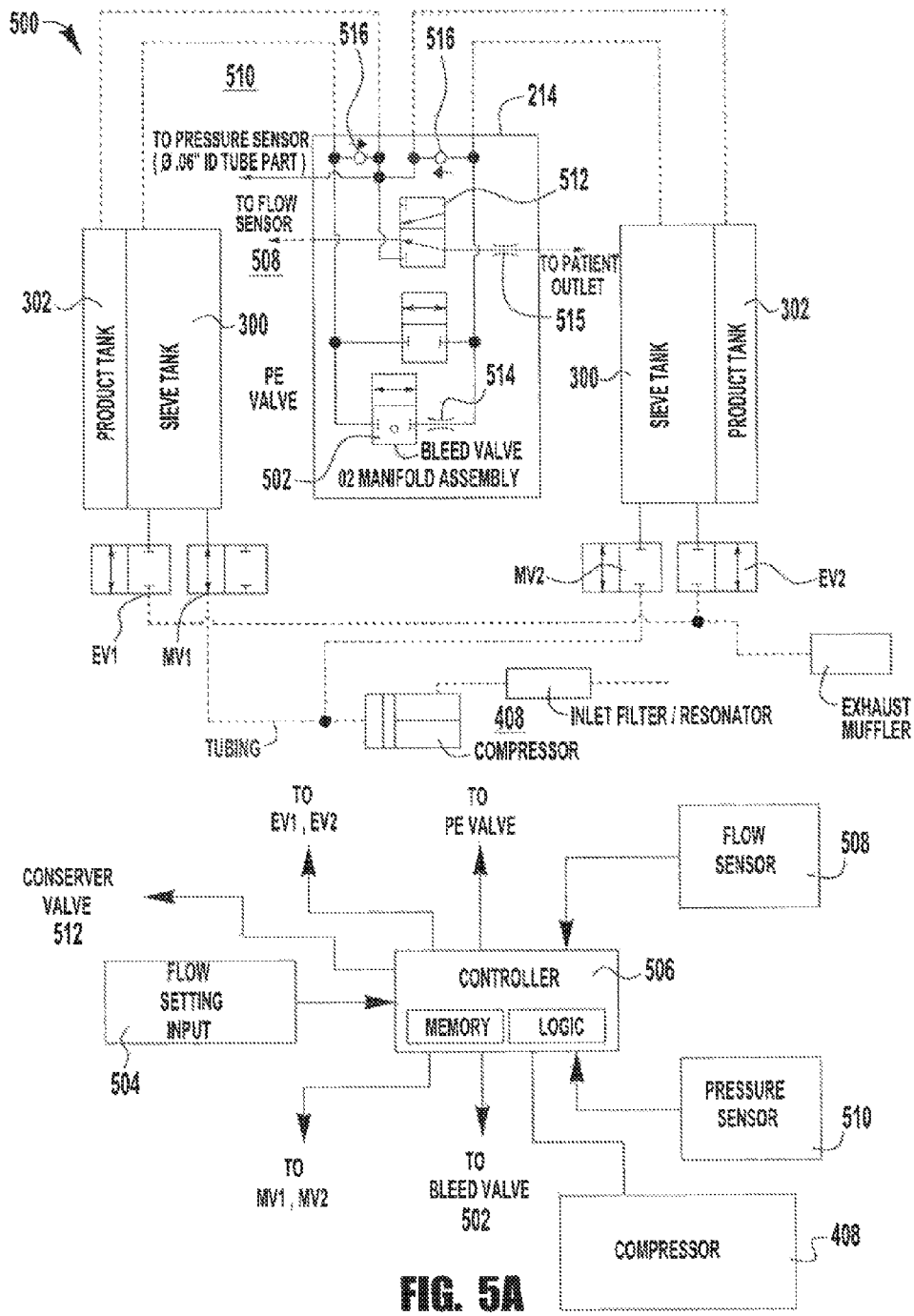
Figure 5C:
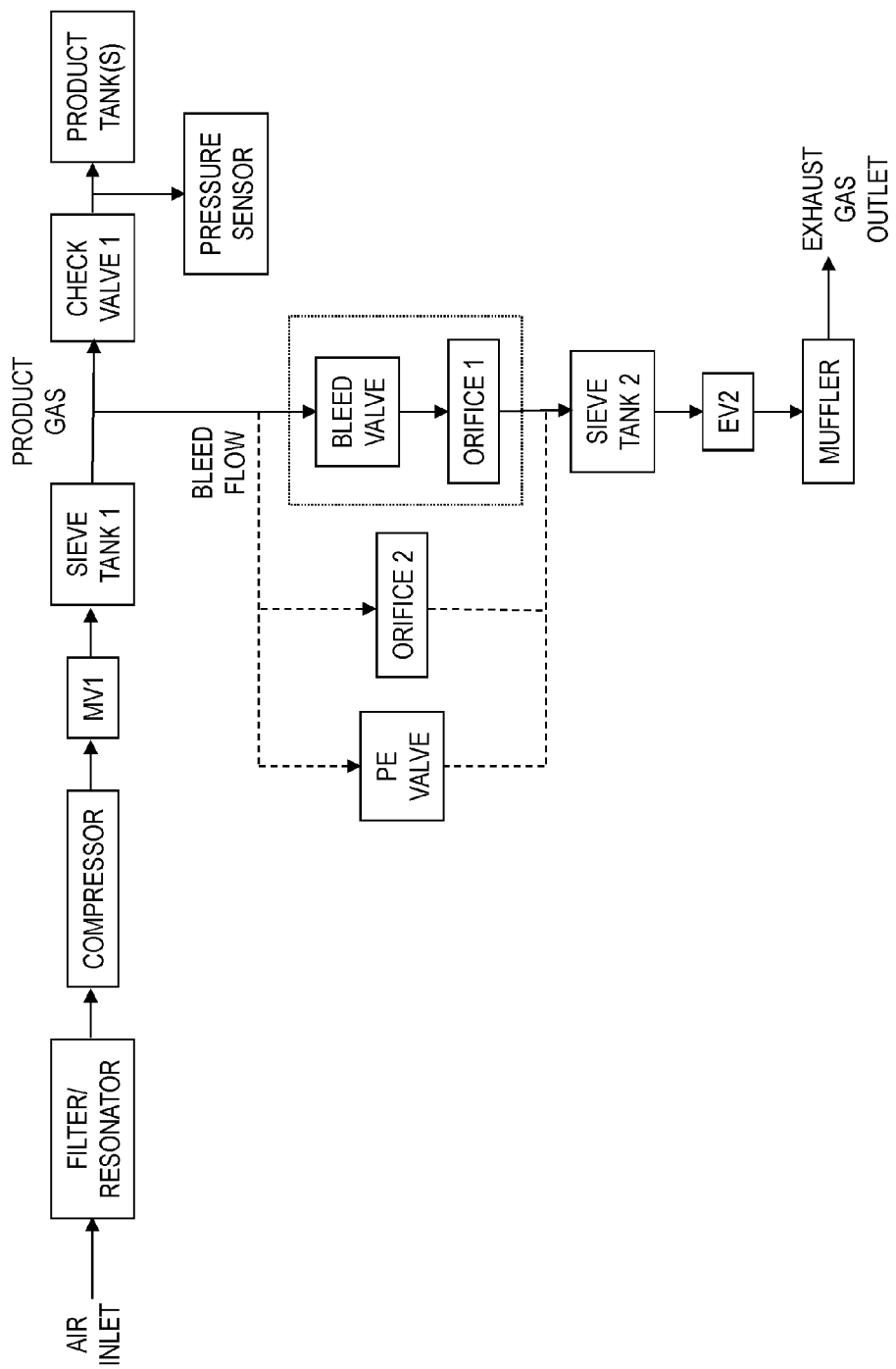
Figure 5D:
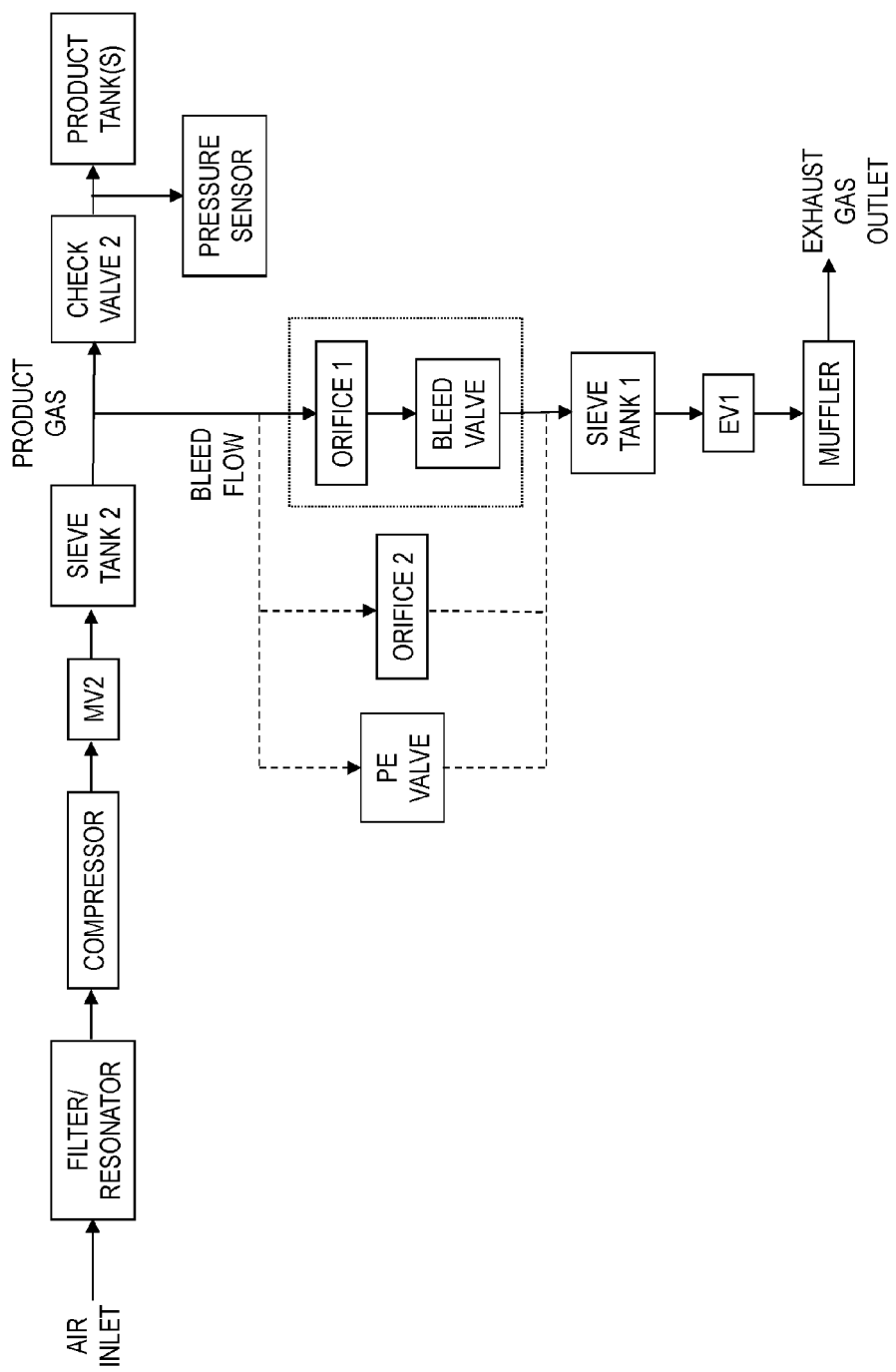
Figure 5E:
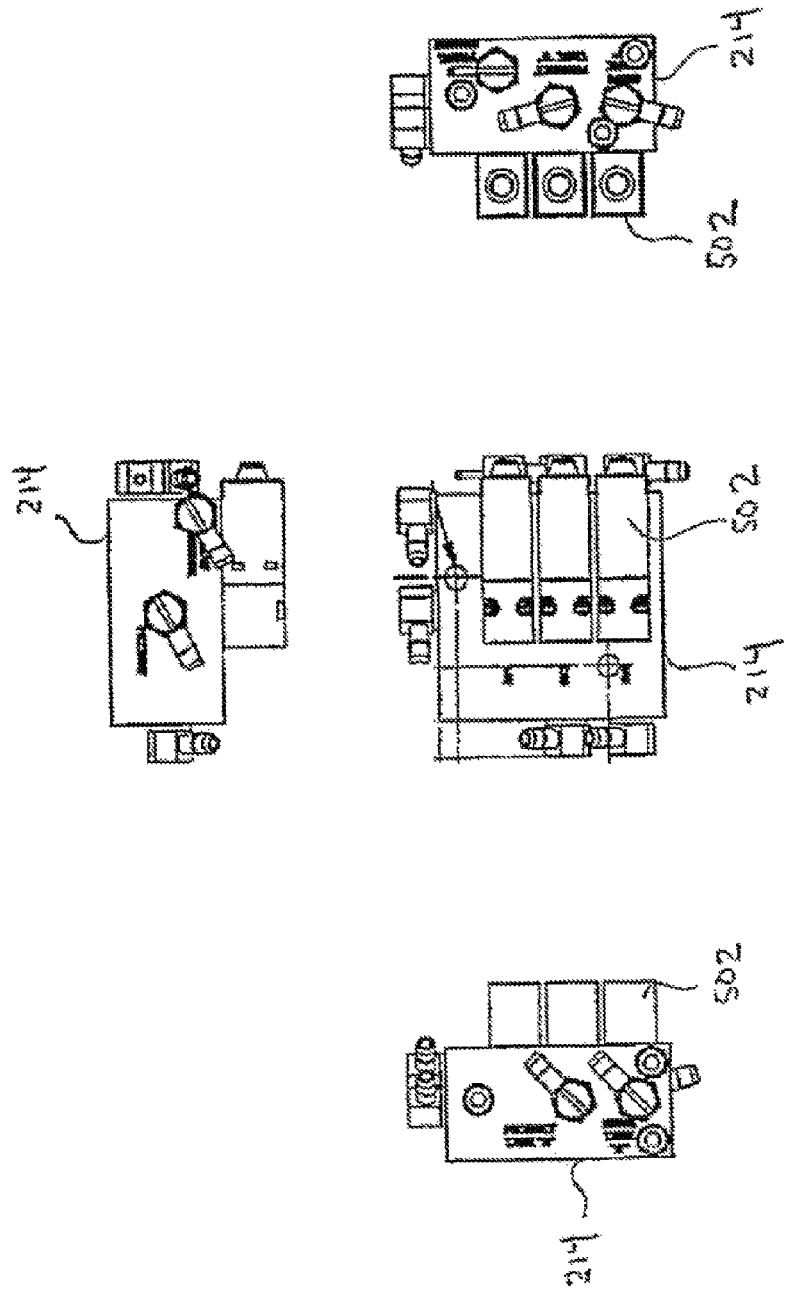
Figure 5F:
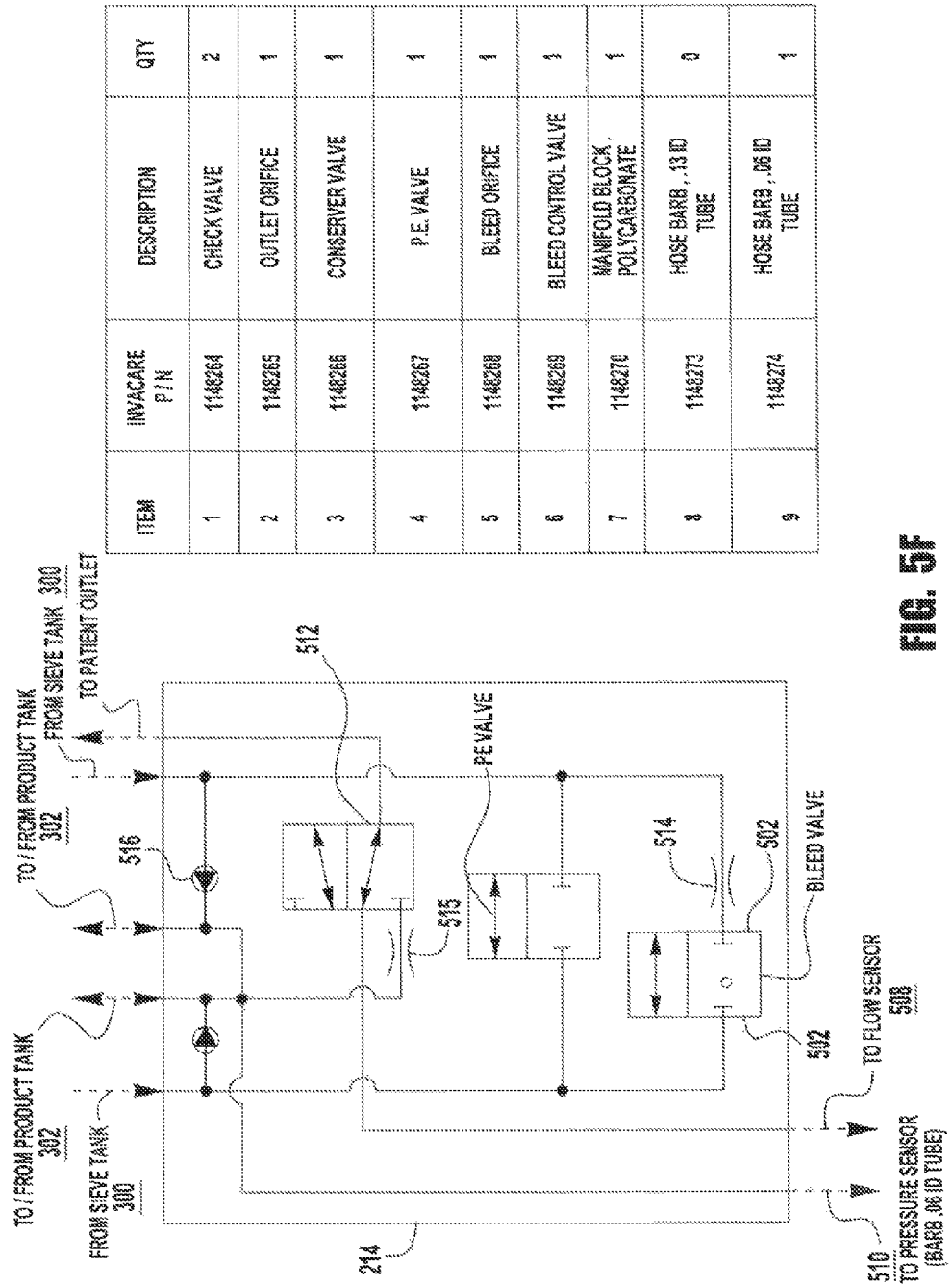
Figure 6A:
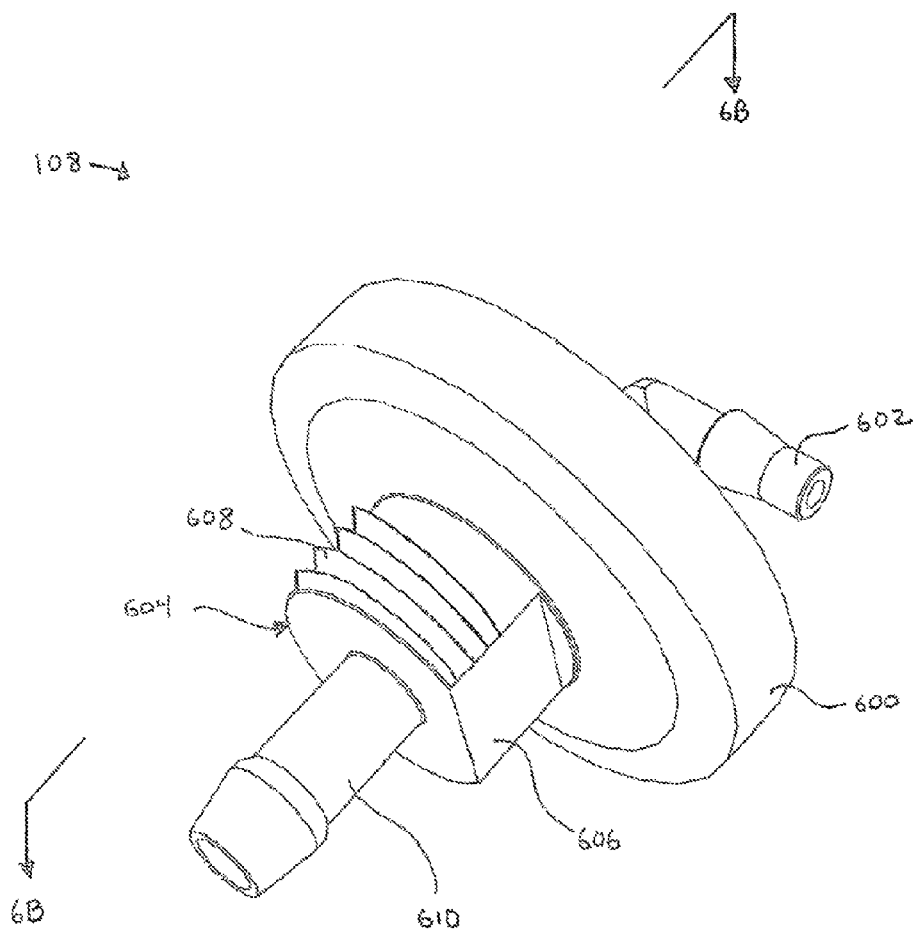
Figure 7:
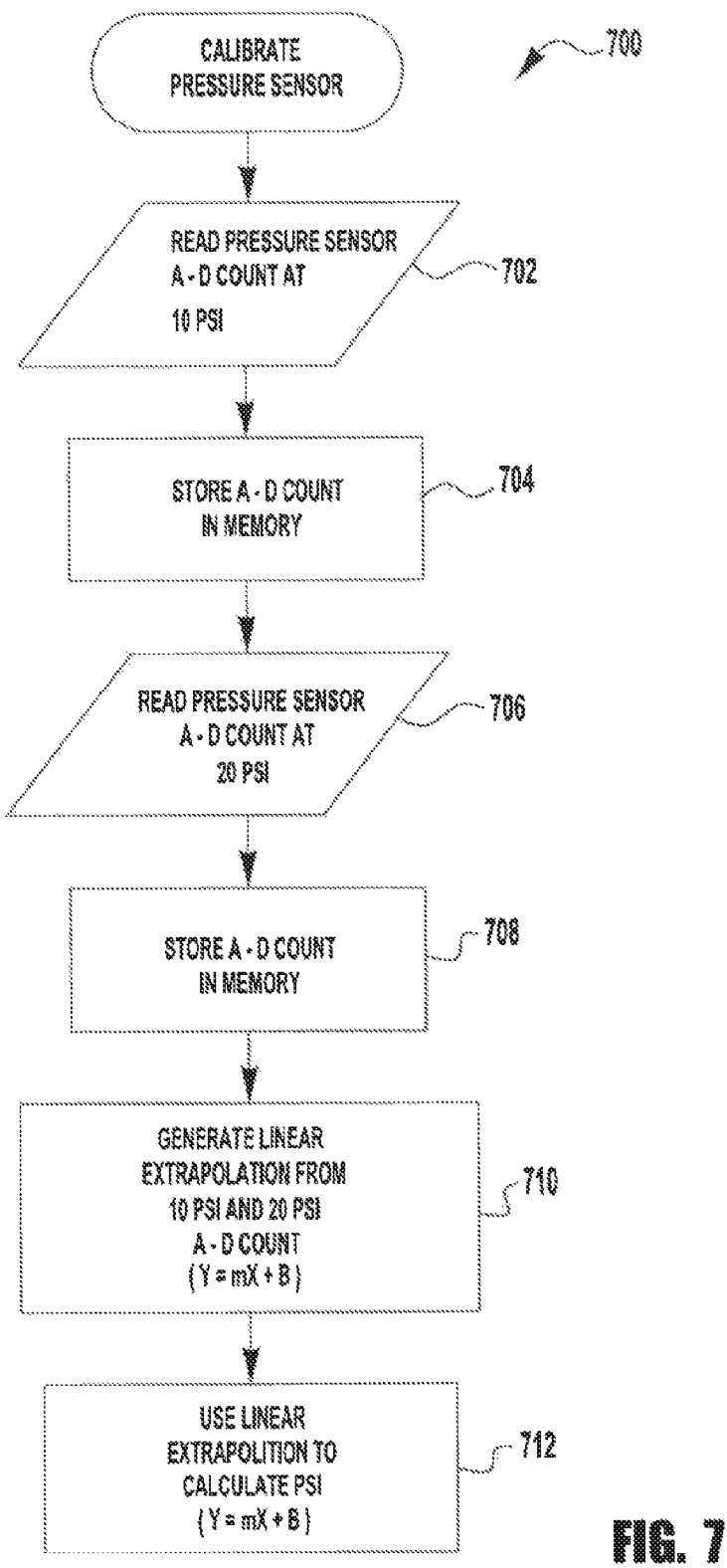
Figure 8:
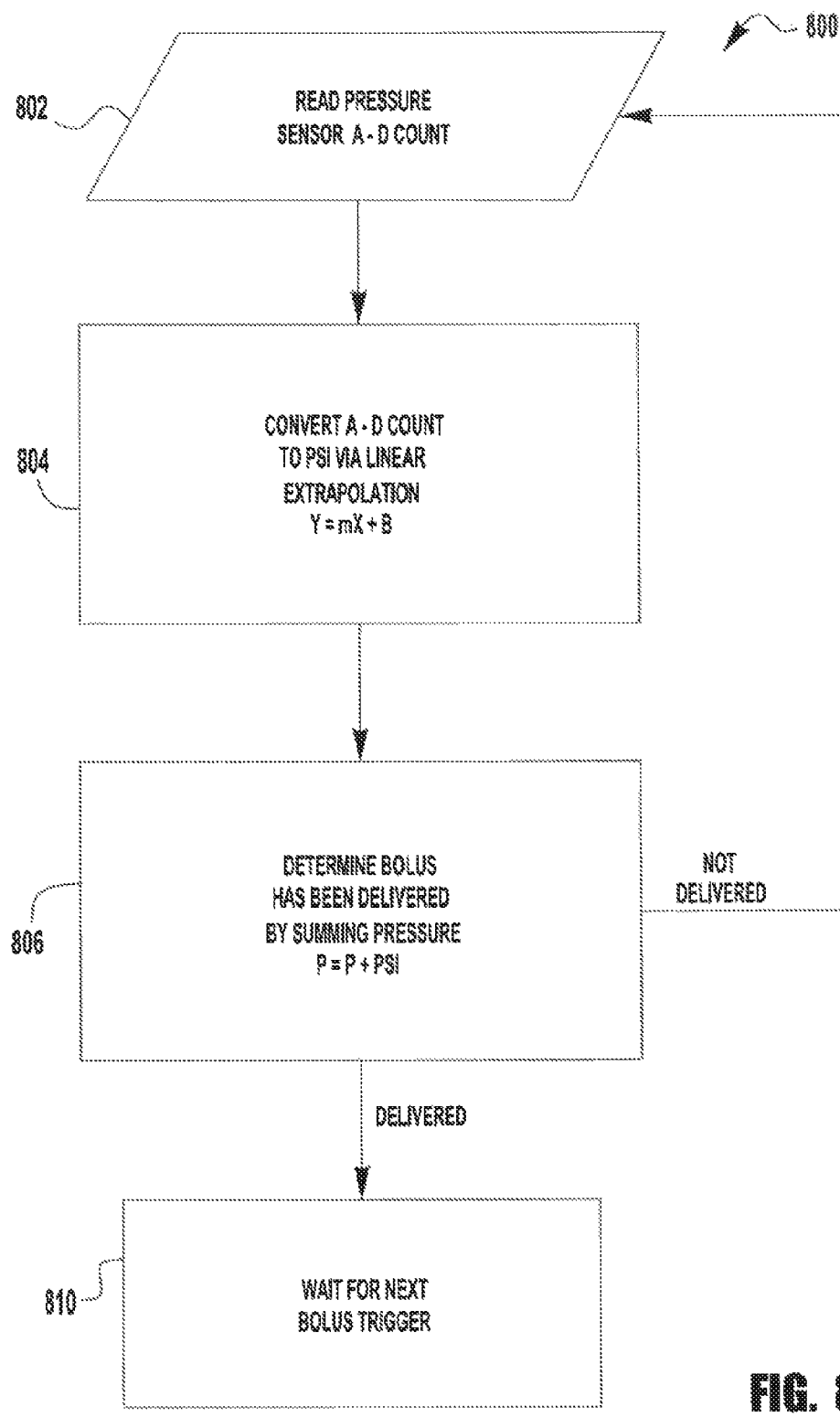
Figure 9:
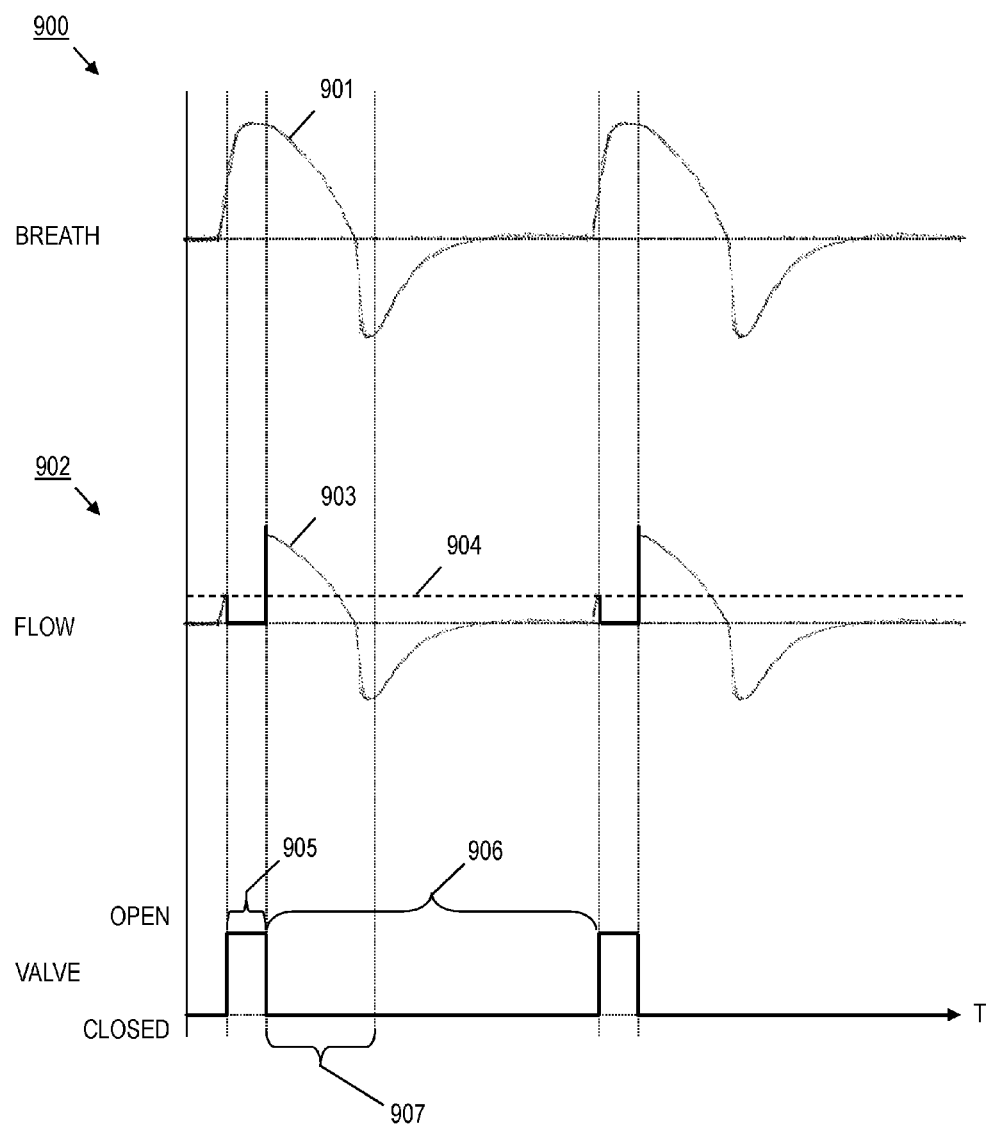
Figure 10:
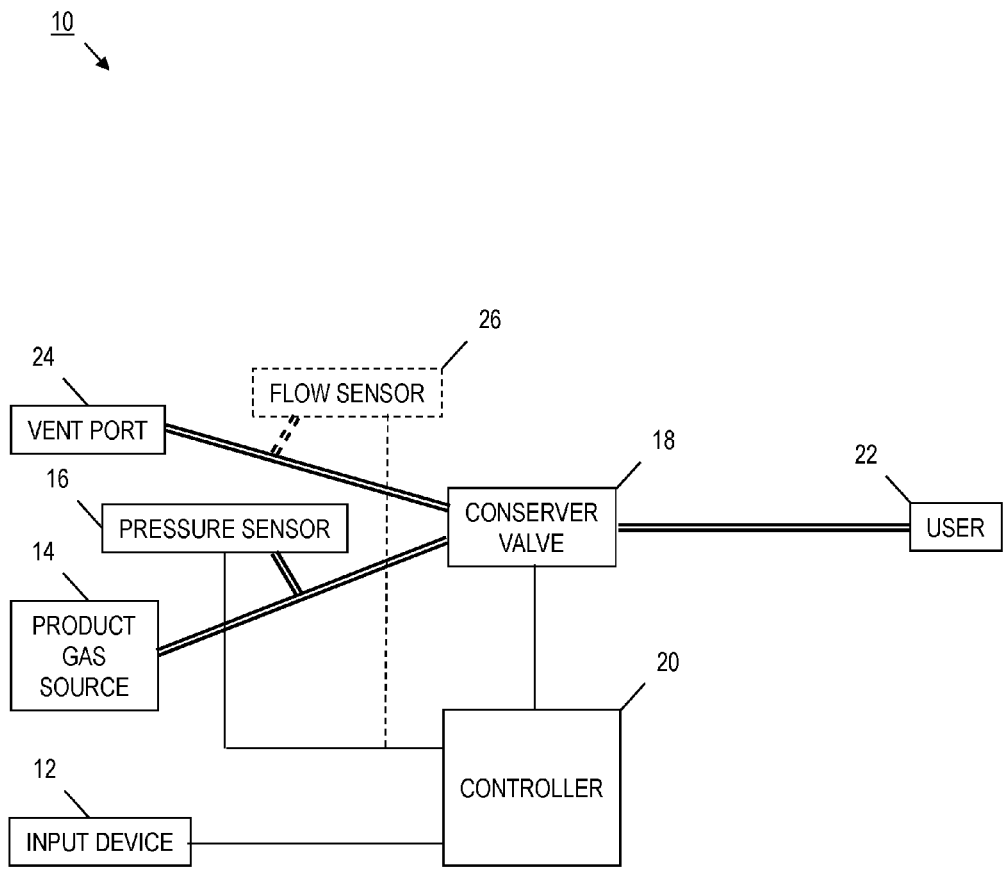
Figure 11:
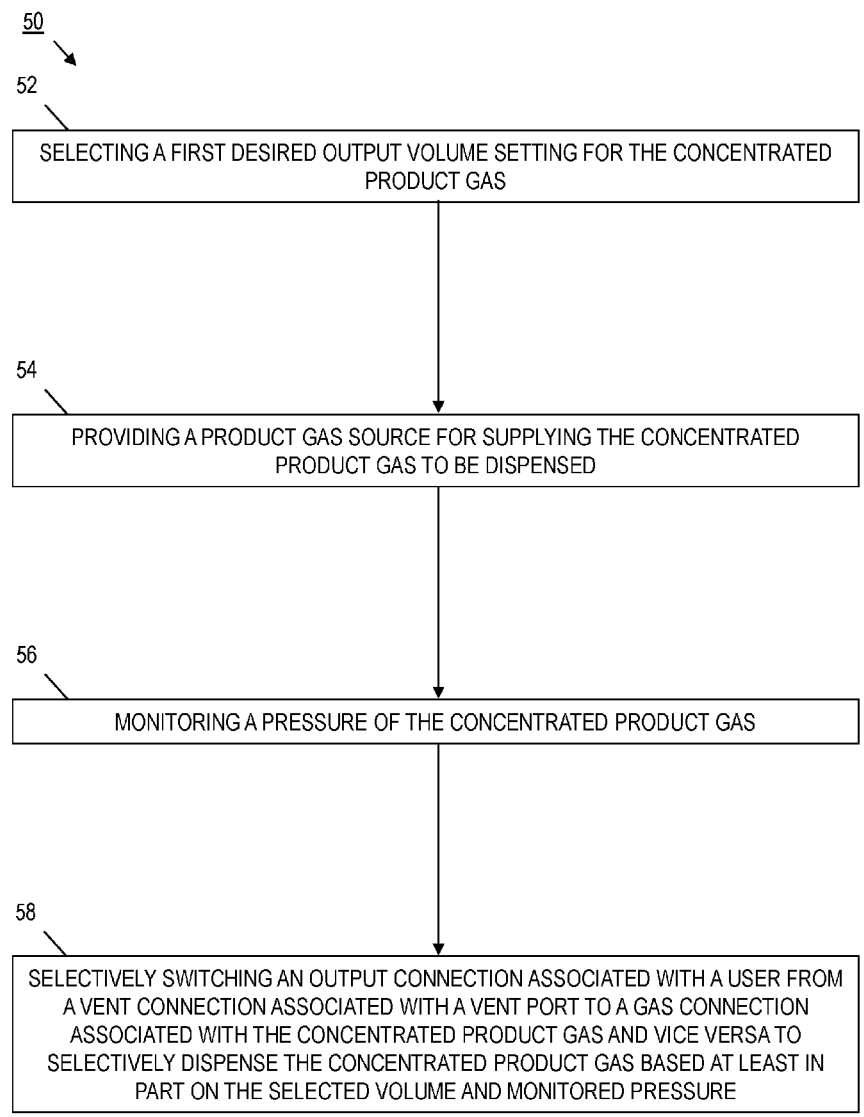

FIG. 1 provides a perspective view of an exemplary embodiment of a product gas concentrator;

FIG. 2 provides an exploded view of the product gas concentrator of FIG. 1;

FIGS. 3A-H provide various perspective, sectional, exploded views of an exemplary embodiment of a sieve bed and product tank assembly for an exemplary product gas concentrator;

FIGS. 3I-O provide various perspective, sectional, exploded views of an alternate exemplary embodiment of an end cap for the sieve bed and product tank assembly of FIG. 3A;

FIGS. 4A-D provide various perspective, sectional, exploded views of an exemplary embodiment of a compressor assembly for an exemplary product gas concentrator;

FIG. 4E provides a top view of an alternate exemplary embodiment of a plurality of suspension links for the compressor assembly of FIG. 4A;

FIG. 4F provide a perspective view of another exemplary embodiment of a compressor assembly for an exemplary product gas concentrator;

FIG. 5A provides several block diagrams of an exemplary embodiment of another product gas concentrator;

FIG. 5B provides a timing diagram for an exemplary embodiment of a valve control scheme for the product gas concentrator of FIG. 5A;

FIG. 5C provides a block diagram showing several exemplary strategies for bleed flow from sieve tank 1 to sieve tank 2 in an exemplary embodiment of an exemplary product gas concentrator;

FIG. 5D provides a block diagram showing several strategies for bleed flow from sieve tank 2 to sieve tank 1 in an exemplary embodiment of an exemplary product gas concentrator;

FIG. 5E provides top and side views of an exemplary embodiment of a valve assembly for the product gas concentrator of FIG. 5A;

FIG. 5F provides a block diagram of the valve assembly of FIG. 5E;

FIGS. 6A and B provide perspective and sectional views of an exemplary embodiment of an output port for an exemplary product gas concentrator;

FIG. 7 provides a flow chart of an exemplary embodiment of a process for determining pressure in relation to an exemplary pressure sensor in an exemplary product gas concentrator;

FIG. 8 provides a flow chart of an exemplary embodiment of a process for determining a time duration for dispensing a bolus of concentrated product gas in an exemplary product gas concentrator;

FIG. 9 provides a timing diagram for an exemplary embodiment of a conserver valve control scheme for an exemplary product gas concentrator;

FIG. 10 provides a block diagram of still another exemplary embodiment of a product gas concentrator; and FIG. 11 provides a flow chart of an exemplary embodiment of a process for dispensing a concentrated product gas to a user in conjunction with a product gas concentrator.

DESCRIPTION

Illustrated in FIG. 1 is one embodiment of an oxygen concentrator 100. Oxygen concentrator 100 includes a housing 102 having a front portion 104 and a rear portion 106. Front and rear portions 104 and 106 include a plurality of openings for the intake and discharge of various gases such as, for example, the intake of room air and the discharge of nitrogen and other gases. Oxygen concentrator 100 generally intakes room air, which is mostly comprised of oxygen and nitrogen, and separates the nitrogen from the oxygen. The oxygen is stored in a storage tank and the nitrogen is discharged back into the room air. For example, the oxygen gas may be discharged through port 108 a patient through tubing and nasal cannula.

FIG. 2 is an exploded perspective of the oxygen concentrator 100 of FIG. 1. Oxygen concentrator 100 further includes a central frame 202 having a circuit board and other components connected thereto. These components include a battery pack 204, sieve bed and product tank assemblies 206 and 208, cooling fan 212, and valve assembly 214. While these components are described as being connected to central frame 202 that need not be the case. One or more of these components may be connected to housing portions 104 or 106. Other components are also housed within oxygen concentrator 100 including, for example, compressor assembly 210, sound attenuators or mufflers 216 and 218 and inlet filter 220.

Sieve Bed and Product Tank Assembly

Figure 3B:
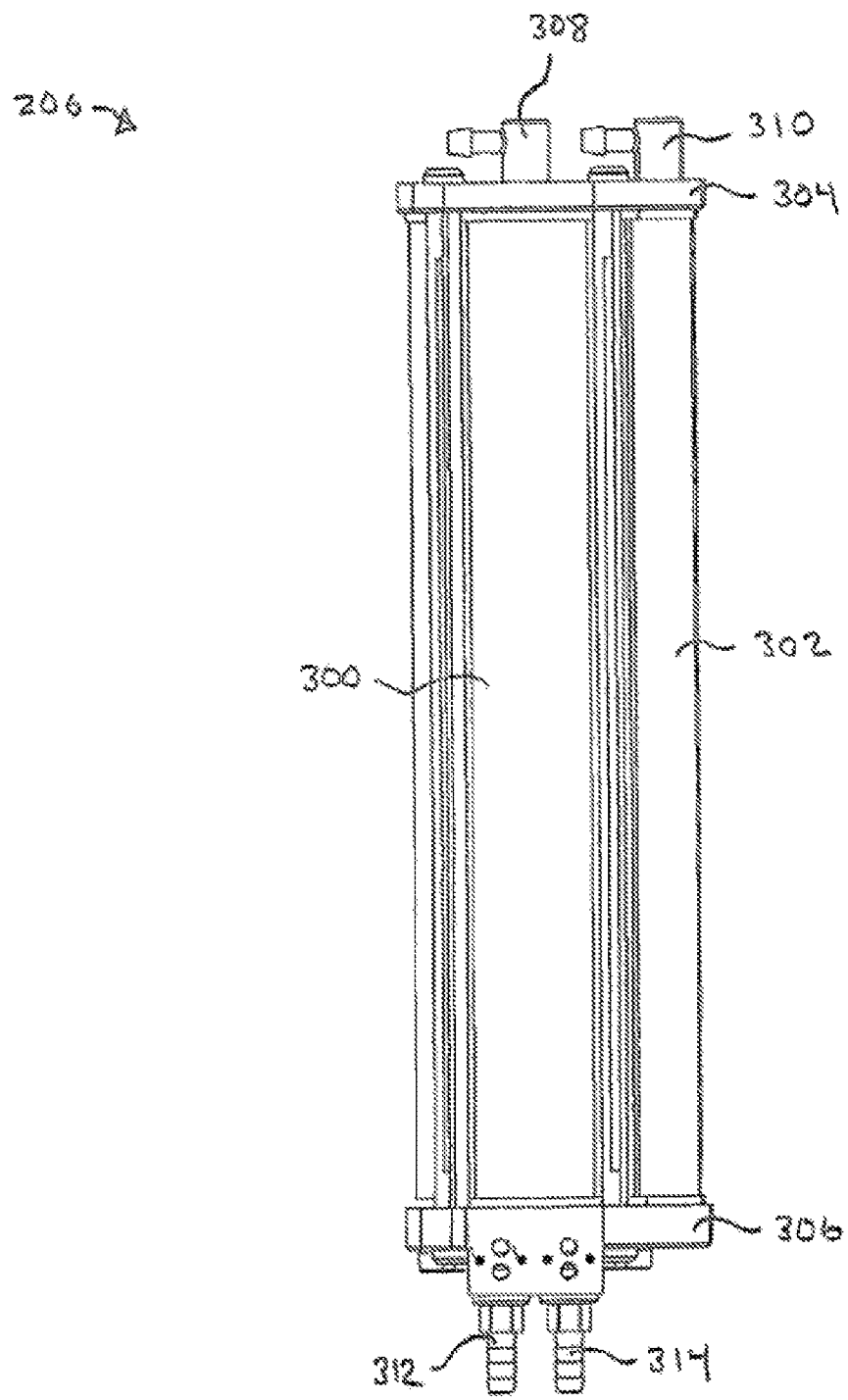

Referring now to FIGS. 3A and 3B, and more particularly to the perspective view FIG. 3A, sieve bed and product tank assembly 206 is shown. Sieve bed and product tank assembly 208 is similarly configured and will not be described separately. Assembly 206 includes a body having a sieve bed portion 300 and a product tank portion 302. The distal ends of the body have first and second end caps 304 and 306. End cap 304 includes outlet ports 308 and 310. Outlet port 308 is associated with the sieve bed portion 300 and outlet port 310 is associated with the product tank portion 302. End cap 306 includes input ports 312 and 314. Input port 312 is associated with sieve bed portion 300 and input port 314 is associated with product tank portion 302. End caps 304 and 306 are suitably connected to the body of assembly 206 with fasteners such as screws or bolts, although any other suitable attachment means may also be used.

Figure 3C:
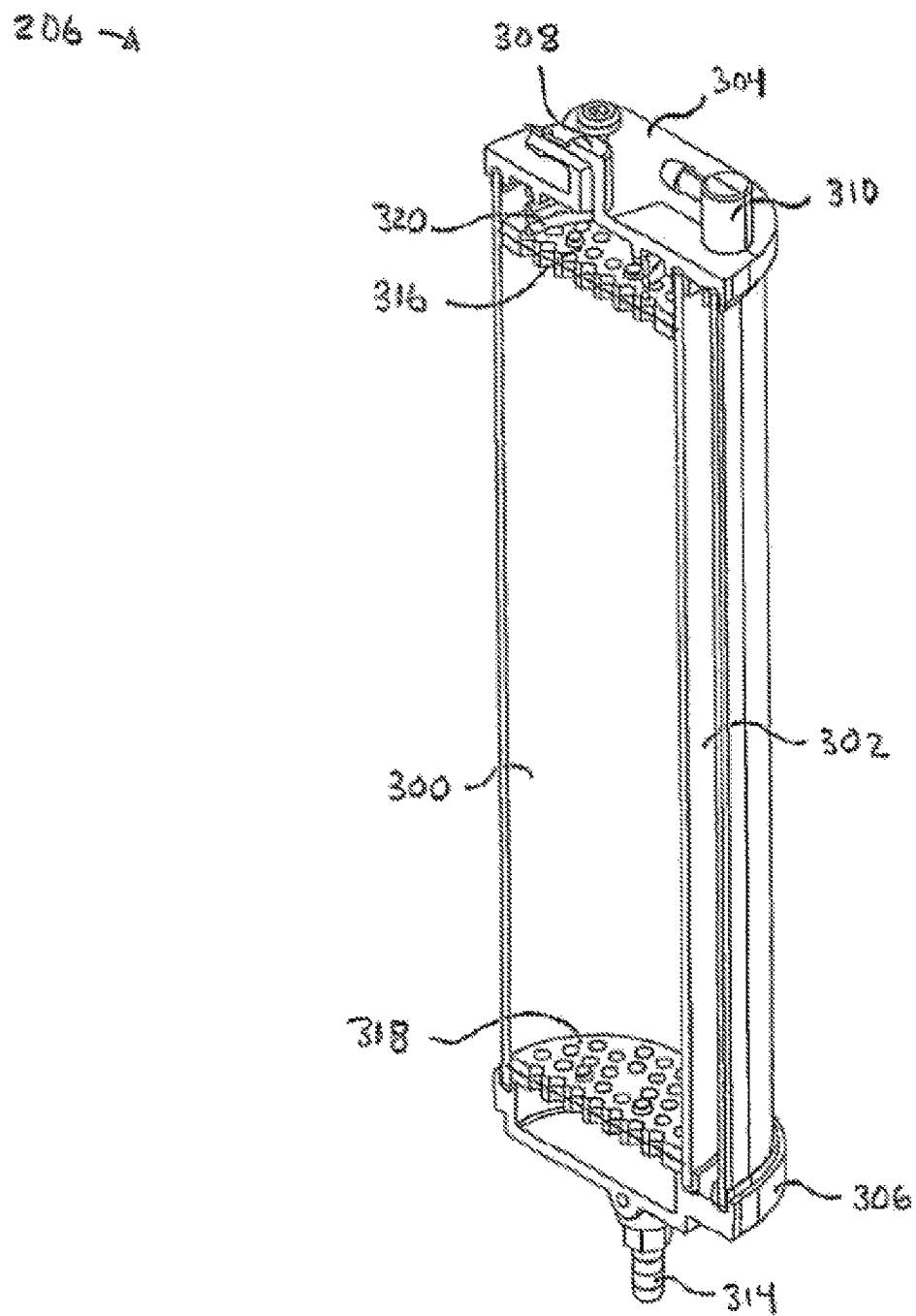
Figure 3D:
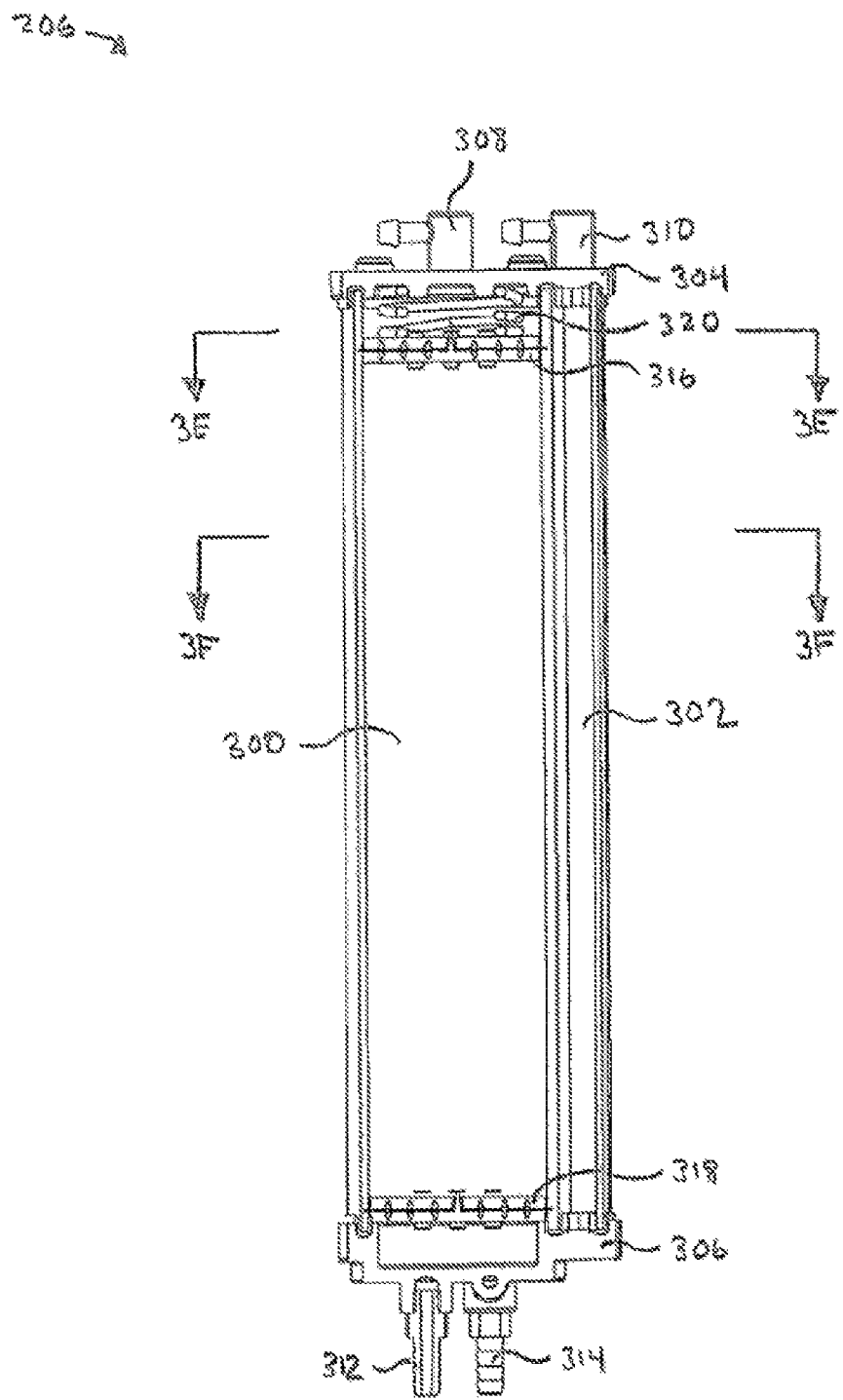

FIGS. 3C and 3D illustrate section views taken along section lines 3C-3C and 3D-3D of FIG. 3A. Sieve bed portion 300 includes first and second perforated inserts 316 and 318. A spring 320 is also provided and presses against insert 316, which in turn presses against the separation medium disposed between inserts 316 and 318. This insures that the physical separation medium is compressed between the inserts 316 and 318.

The space between perforated inserts 316 and 318 is filled with a physical separation medium or material. The separation material selectively adsorbs one or more adsorbable components of a gaseous mixtures such as, for example, a gaseous mixture of nitrogen and oxygen, and allows one or more nonadsorbable components of the gaseous mixture to pass. The physical separation material is a molecular sieve with pores of uniform size and essentially the same molecular dimensions. These pores selectively adsorb molecules in accordance with molecular shape, polarity, degree of saturation, and the like. In one embodiment, the physical separation medium is an aluminasilicate composition with 4 to 5 angstrom pores. In this embodiment, the molecular sieve is a sodium or calcium form of aluminasilicate, such as type 5A zeolite. Alternately, the aluminasilicate may have a higher silicon to aluminum ratio, larger pores, and an affinity for polar molecules, e.g. type 13x zeolite. In another embodiment, a lithium-based zeolite may be used. In other embodiments, any suitable zeolite or other adsorbent material. The zeolites adsorb nitrogen, carbon monoxide, carbon dioxide, water vapor, and other significant components of air. Gases such as oxygen that have not been adsorbed in sieve bed portion 300 are collected and stored in product tank portion 302.

Figure 3E:
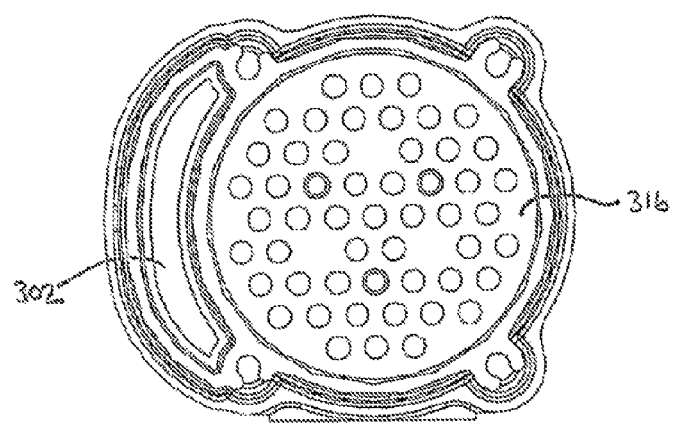
Figure 3F:
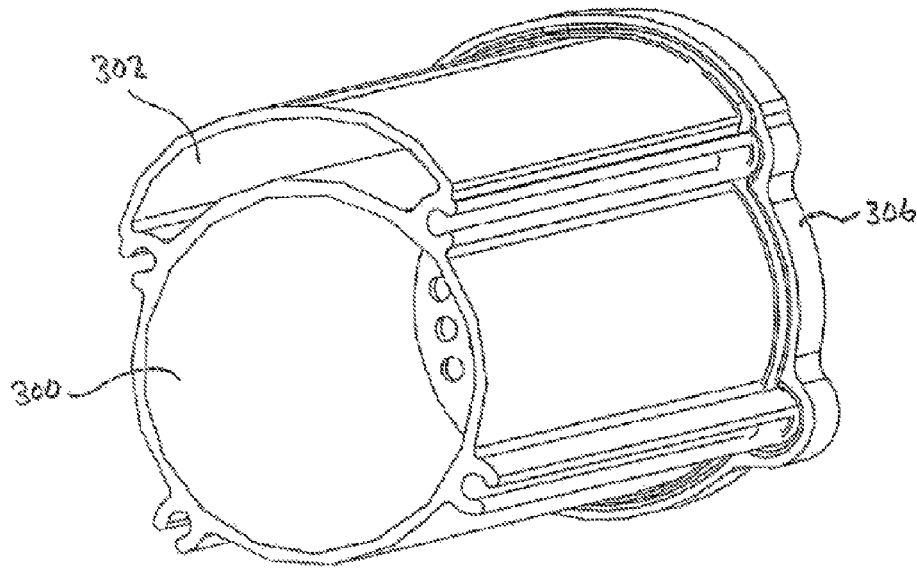

FIG. 3E is a section view taken along line 3E-3E of FIG. 3D. Product tank portion 302 and insert 316 of sieve bed portion 300 are illustrated. FIG. 3F is a further section view along line 3F-3F of FIG. 3D and is shown in perspective. As illustrated in this embodiment, sieve bed portion 300 and product tank portion 302 are formed from a single extruded piece of material such as, for example, aluminum. Other materials capable of being extruded may also be used.

Sieve bed portion 300 and product tank portion 302 share a common wall portion and form an integrated sieve bed and product tank assembly. In particular, the inner spaces of sieve bed portion 300 and product tank portion 302 are at least partially bounded by a common wall structure. In this embodiment, the common wall structure is shown as a portion of an arcuate or curved wall that is shared by sieve bed portion 300 and product tank portion 302. In other embodiments, the common wall structure need not be arcuate or curved and can be linear or any other shape. Furthermore, other structures capable of being extruded may join otherwise separate sieve bed portions and product tank portions including, for example, web(s), projections, or extensions.

Still further, more than one sieve bed portion 300 and one product tank portion 302 many be formed by extrusion and connected as described herein. For example, sieve bed portion 300 shown in FIG. 3F may share a common wall structure with multiple product tank portions 302, which may partially or fully circumscribe sieve bed portion 300 in the same manner as product tank portion 302. Similarly, product tank portion 302 may share a common wall structure with multiple sieve bed portions 300.

Figure 3G:
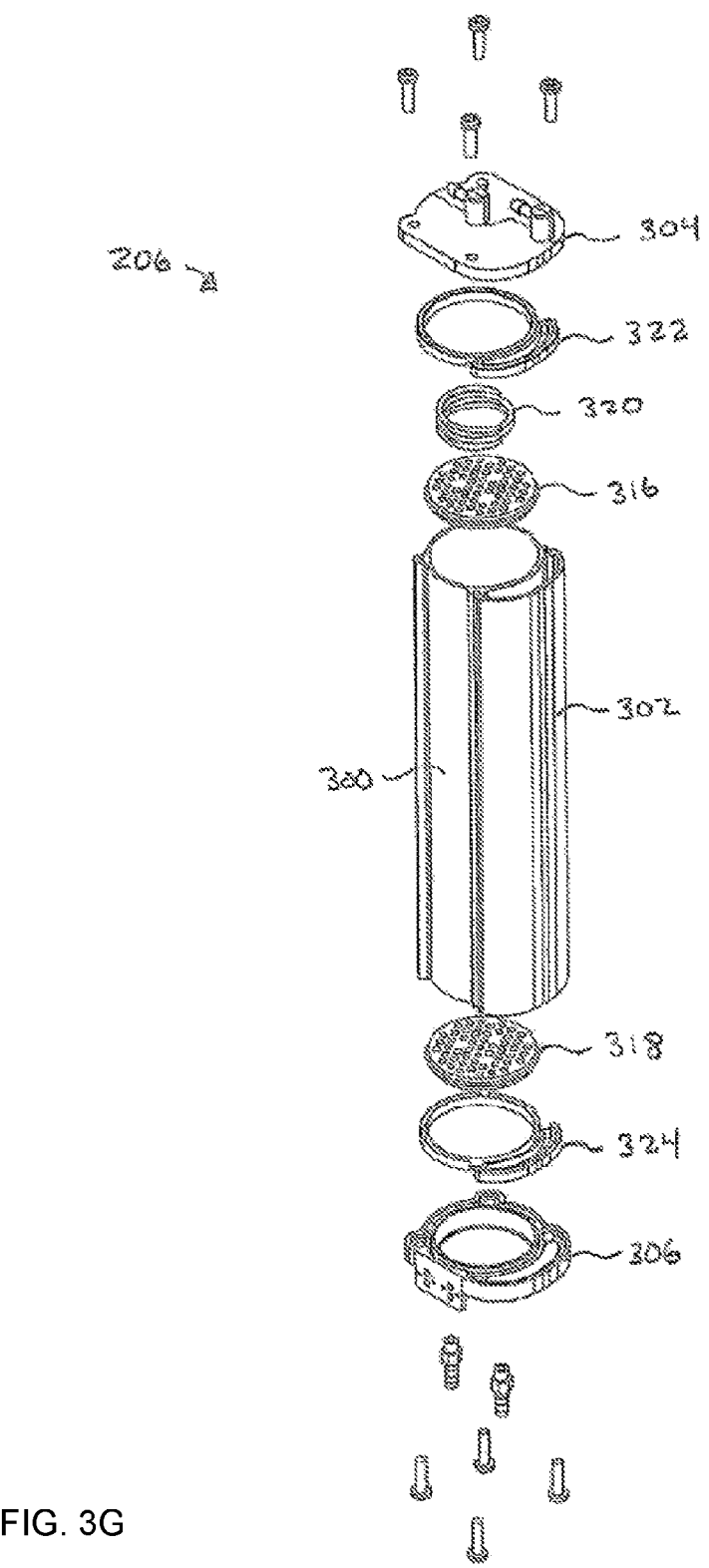

Referring to now to FIG. 3G, an exploded perspective view of sieve bed and product tank assembly 206 is shown. As described earlier, assembly 206 includes end caps 304 and 306, which attach to sieve bed portion 300 and product tank portion 302. The attachment of end caps 304 and 306 is facilitated through seal members 322 and 324. As shown in FIG. 3G, seal members 322 and 324 have a physical geometry that matches the cross-section of the distal ends of sieve bed portion 300 and product tank portion 302. Seal members 322 and 324 are configured to receive the ends of sieve bed portion 300 and product tank portion 302. Seal members 322 and 324 are also configured to be received within a mating portion of end caps 304 and 305. In this manner, seal portions 322 and 324 provide a gasketing effect facilitating attachment of end caps 304 and 306 and sealing of the inner spaces of sieve bed portion 302 and product tank portion 304. Each seal portion includes components for sealing the sieve bed portion 300 and product tank portion 302. In other embodiments, seal members 322 and 324 may be omitted by providing a sealing portion within end caps 304 and 306.

Figure 3H:
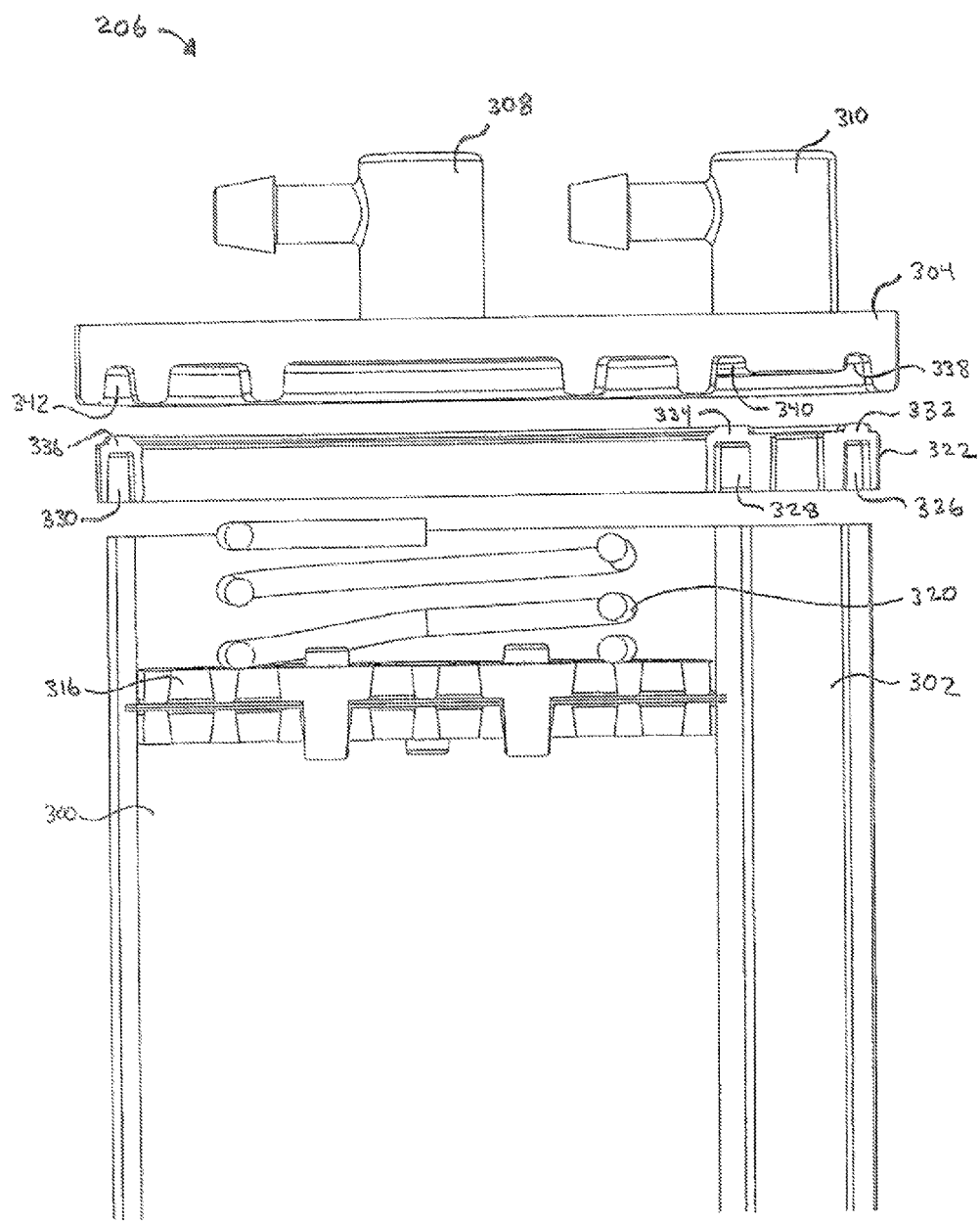

FIG. 3H is a detail view of the upper portion of sieve bed and product tank assembly 206. Seal member 322 includes a plurality of recesses 326, 328, and 330, for example, for receiving the ends of sieve bed portion 300 and product tank portion 302. Each recess is walled and includes top portions 332, 334, and 336, for example. Top portions 332, 334, and 336 of seal member 322 are received within recesses 338, 340, and 342, for example, of end cap 304. End cap 304 recesses 338, 340, and 342, for example, are formed by walls that project from end cap 304. When end cap 304 is secured to sieve bed portion 300 and product tank portion 302 via fasteners, end cap 304 and sieve bed portion 300 and product tank portion 302 compress seal member 322 thereby providing a gas-tight seal. End cap 306 and seal member 324 are similarly configured. As described above, seal members 322 and 324 can be omitted and recesses 338, 340 and 342 in end cap 304 can be made to form a gas-tight seal.

Figures 3I, 3J:
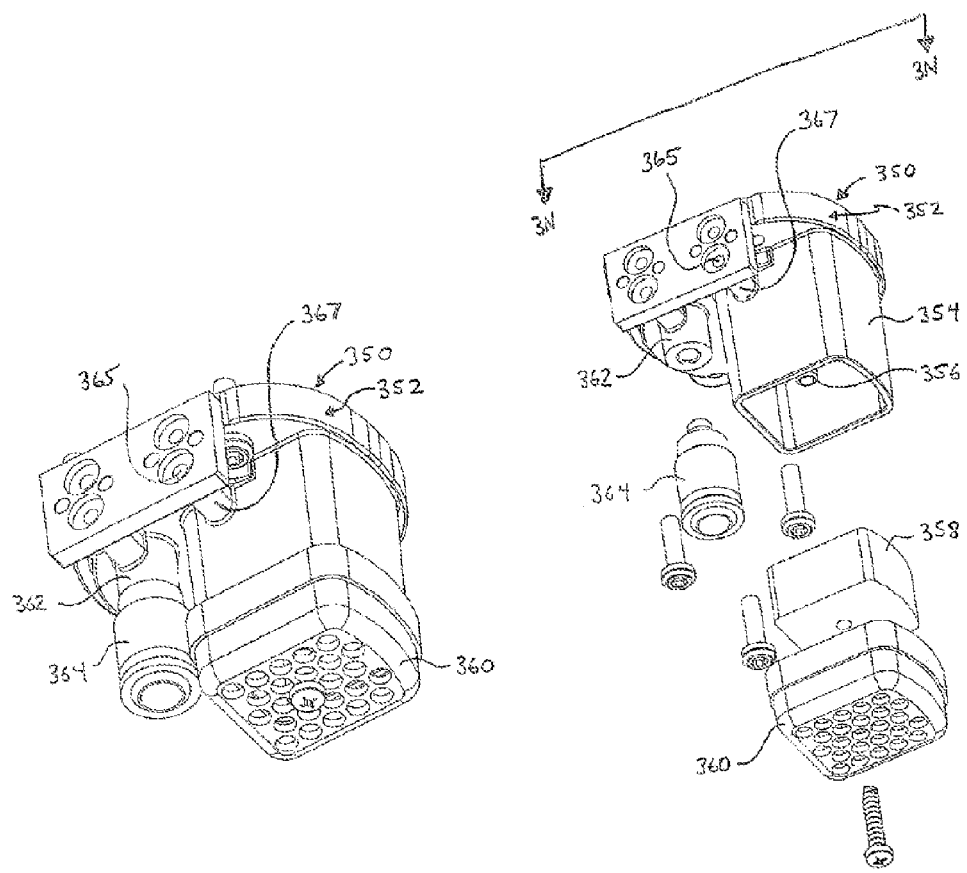

Referring to now to FIGS. 3I-3L, and more particularly to FIG. 3J, perspective views of an alternate end cap design 350 is shown. End cap 350 differs from the previously described end cap 304 in that it includes an integrated sound attenuator or muffler. Whereas the embodiment of FIG. 2 includes discreet sound attenuators or mufflers 216 and 218, the embodiment of end cap 350 integrates a sound attenuator or muffler into its structure.

As shown in FIG. 3J, end cap 350 includes a body having a sieve bed/product tank interface portion 352. Interface portion 352 also serves as a base from which muffler portion 354 extends. Also extending from interface portion 352 is a mounting boss 356. A muffler block 358 is housed within muffler portion 354 and a perforated exhaust cap 360 closes muffler portion 354. Mounting boss 356 accepts a fastener that passes through exhaust cap 360 and muffler block 358. Alternative means for securing these components can also be utilized.

End cap 350 further includes an input port 362 and a fitting 364 that may be attached to it. End cap 350 also includes an input port 365 to the muffler portion 354. Input port 365 is connected to muffler portion 354 through passageway 367. In this manner, gases exhausted from the sieve bed are input through port 365 and passageway 367 into muffler portion 354. The gases are then exhausted by muffler portion 354 through perforated end cap 360.

Figure 3M:
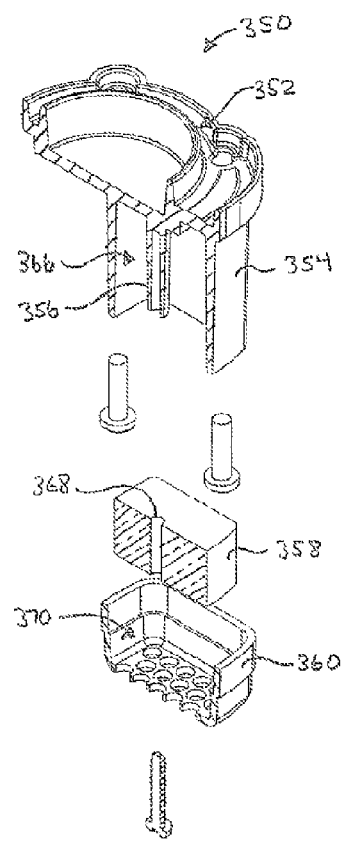
Figure 3N:
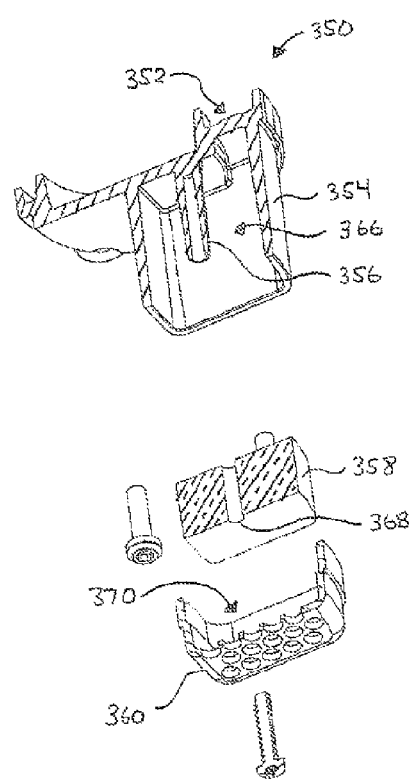

Referring now to FIGS. 3M and 3N, and particularly to FIG. 3N, an exploded sectional view of end cap 350 is shown. Sieve bed/product tank interface portion 352 is shown having walled structures similar to end cap 304 for accepting a seal member similar to seal member 322 (See FIG. 3F and its accompanying text). Muffler portion 354 has walls that extend from interface portion 354 so as to form a perimeter bounding space 366. Mounting boss 356 also extends from interface portion 352 and resides in space 366.

Figure 3O:
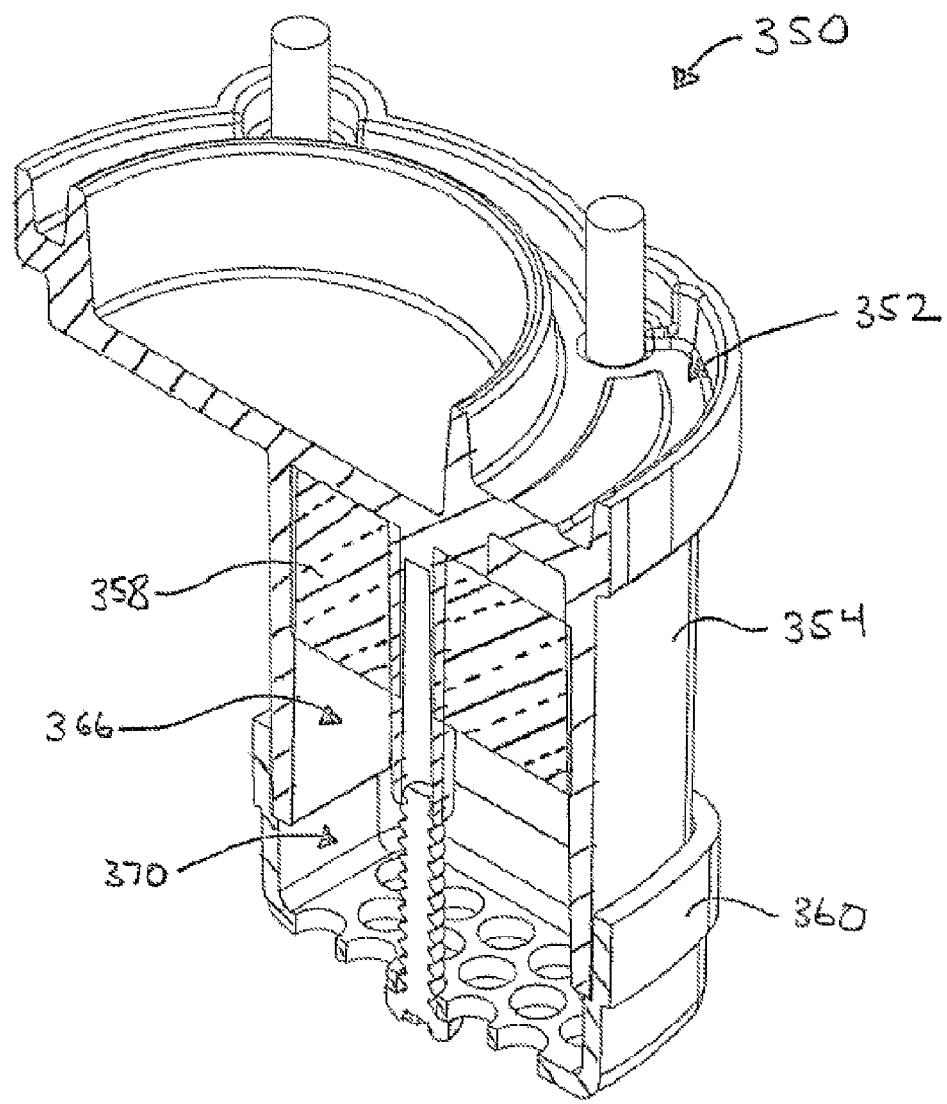

Muffler block 358 is porous and includes a bore or hole 368 extending therethrough. The bore or hole 368 is sized so that mounting boss 356 can be received therein to hold and retain muffler block 358. In other embodiments, muffler block 358 can be semi-porous having non-porous portions or can be made of any other sound-deadening material. Muffler block 358 is disposed proximate interface portion 352 within space 366, though it can sized so as to at least partly fill space 366. As gases are exhausted, muffler block 358 may be displaced so as to reside more proximate or against perforated cap 360 (see FIG. 3O showing un-displaced position).

Perforated cap 360 includes a plurality of holes for exhausting gases introduced into muffler portion 354. Cap 360 includes a base portion having the holes and walls that extend therefrom so as to form a space 370. End cap 360 and its walls are structured to receive an end section of muffler portion 354 therein. This is accomplished by providing the walls of cap 360 with a shoulder portion for abutting against the end section of the muffler portion 354. A fastener then passes through cap 360 and interfaces with boss 356 to hold the two components together. Other means of fastening can also be used including snap clips, glue, ultrasonic welding, etc. FIG. 3O shows a cross-sectional perspective of end cap 350 illustrating the assembled structure.

Compressor Assembly

Referring to now to FIG. 4A, a perspective view of compressor assembly 210 and rear housing portion 106 is shown. Compressor assembly 210 has frame 406 within which compressor 408 is mounted or suspended. Rear housing portion 106 has slots 400 and 402 that interface with the compressor assembly 210. Frame 406 has tabs such as, for example, tab 404, which are received in slots 400 and 402 to locate and secure the compressor assembly 210 to the rear housing portion 106. Other means of mounting compressor assembly 210 to rear housing portion 106 can also be employed such as, for example, brackets and fasteners.

FIG. 4B is an exploded perspective view of the compressor assembly 210. Compressor assembly 210 includes compressor 408, a multi-piece interface bracket having members 420, 422, and 424, frame 406, and a plurality of suspension members 430. Interface bracket member 420 includes a plurality of hook-type portions 428 that couple with apertures 426 in interface bracket members 422 and 424. FIG. 4C illustrates the interface bracket when members 420, 422 and 424 are coupled together. The interface bracket is coupled or affixed to a body of compressor 408 through appropriate fastening means such as, for example, screws, bolts, clips, or pins.

Still referring to FIG. 4B, suspension members 430 include enlarged end portions that are connected together through elongated central portions. Suspension members 430 are resilient in that they can be stretched under tension. In one embodiment, suspension members 430 are formed from an elastomeric material such as, for example, rubber. In other embodiments, suspension members 430 can be made of metal to form resilient springs.

Frame 406 includes a plurality of structural support members generally forming a cage-like structure having a top 414, bottom 416, and sides 412 and 418. The corner portions of frame 406 include openings or apertures 434 that are used in conjunction with suspension members 430 to mount or suspend compressor 408 within frame 406 as shown in FIG. 4A.

Referring now to FIG. 4D, a sectional view of compressor assembly 210 with compressor 408 removed is shown. Interface bracket member 424 is shown and includes hook portions 432 that interface with suspension members 430. In particular, the enlarged end portions of suspension members 430 are inserted within the eye of hook portions 432 and the recesses or openings 434 of frame 406. While FIG. 4D illustrates the suspension or mounting of interface bracket 424 within frame 406, interface bracket 422 is similarly suspended or mounted within the frame 406 thereby suspending or mounting compressor 408 within frame 406.

Configured as such, compressor 408 is suspended or mounted relative to frame 406 in a manner that isolates the movement or vibration of compressor 408. The movement or vibration of compressor 408 is isolated through elastic suspension members 430. Elastic suspension members 430 allow compressor 408 to move within frame 406 without translating that movement to frame 406. In this embodiment, a total of eight suspension members 430 are employed at the corners of frame 406 but this need not to be the case. Any number of suspension members may be used at any location(s) with respect to frame 406 and compressor 408 in a manner that suitably allows compressor 408 to move relative to frame 406 without translating that movement to frame 406.

Referring now to FIG. 4E, a second embodiment of a suspension member is shown in the form of suspension member 436. Suspension member 436 is similar to suspension members 430 in that it structurally incorporates a plurality of suspension members 430. As shown, suspension member 436 incorporates four individual suspension members 430. Suspension member 436 further includes connective portions 438 that connects together the individual suspension member portions 430 to form a unitary whole. In other embodiments, suspension member 436 need not be formed as a continuous structure but may also form an open structure such as, for example, by omitting one of the connective portions 438 shown in FIG. 4E. Another configuration that provides for the physical communication of individual suspension members 430 can also be employed.

Suspension member 436 is connected to interface bracket members 422 and 424 in the same manner as described for the individual suspension members of 430. That is, the enlarged end portions 440 of suspension members 430 are inserted into the eye of hook portions 432 of the interface bracket members and the enlarged end portions 442 are inserted into the openings or recesses 434 of frame 406. It may be that in some cases suspension member 436 allows for easier assembly of compressor assembly 210. In the embodiment shown, two suspension members of 436 would be required to replace the eight suspension members 430 shown in FIG. 4B. FIG. 4F illustrates yet another embodiment of compressor assembly 210 having and interface bracket with circular end portions that are suspended within a frame by suspension members 430.

Configured as such, compressor assembly 210 reduces noise, vibration and vibration induced noise that may emanate from the compressor during operation. Also, compressor assembly is configured that compressor 408 may be mounted within frame 408 according to a plurality of orientations. The interface bracket members 420, 422 and 424 and frame 406 can be made of any suitable material including, for example, metal or plastic or combinations thereof.

Variable Bleed Valve

Another embodiment of a concentrator includes a variable bleed valve 502. Referring now to FIG. 5A, bleed valve 502 and a fixed orifice 514 are in series and in pneumatic communication with sieve tanks 300. In operation, a flow setting input 504 is selected by a user and received by a microprocessor-based controller 506. Controller 506 has associated therewith memory and logic for controlling the operation of, for example, the compressor 408, main valves MV1 and MV2, exhaust valves EV1 and EV2, conserver valve 512, pressure equalization valve PE and bleed valve 502. All of these valves are solenoid controlled. In one embodiment, the compressor 408 is run at a variable speed based on the flow setting input 504. For example, low flow settings allow for the compressor 408 to be run at a slower speed thereby conserving energy. The compressor 408 can be run at higher speeds for higher flow settings. For example, the controller 506 may run the compressor 408 at 1,100 revolutions per minute (rpm), 1,500 rpm, 2,050 rpm, 2,450 rpm, and 3,100 rpm with respect to the lowest to highest flow setting inputs 504. Of course, other speed values are envisioned and any suitable speed value may be implemented. Controller 506 also receives input from a pressure sensor 510.

The flow setting input 504 is received by controller 506. The flow setting input 504 may designate a flow rate that the user desires for delivery of the product gas (e.g., oxygen) in a pulsed output mode. For example, a plurality of flow input settings 504 may include 300 cc/min (e.g., 15 cc/pulse at 20 breaths per minute (bpm)), 460 cc/min (e.g., 23 cc/pulse at 20 bpm), 620 cc/min (e.g., 31 cc/pulse at 20 bpm), 740 cc/min (e.g., 37 cc/pulse at 20 bpm), or 840 cc/min (e.g., 42 cc/pulse at 20 bpm). Based on this setting, controller 506 appropriately controls the compressor 408 and valves to deliver the desired pulsed output flow of oxygen. Of course, other flow rate values are envisioned and any suitable flow rate value may be implemented. Additionally, the flow setting input 504 may designate a flow rate that the user desires for delivery of the product gas in a continuous output mode.

Generally, the concentrator operates using a pressure swing adsorption (PSA) process. The compressor 408 delivers room air, through main valves MV1 and MV2, in an alternate fashion to sieve tanks 300. While one sieve tank 300 is being filled, the other sieve tank 300 is typically being purged of its contents. As described earlier, each sieve tank 300 is filled within a nitrogen adsorbing material so that nitrogen gas is trapped within the sieve tank 300 and oxygen gas is allowed to pass to the product tank 302. When a particular sieve tank has reached its adsorption capacity, which can be known by its output pressure, the adsorbed gases, such as nitrogen, must be purged before the sieve tank 300 can be used again.

Pressure equalization valve PE allows for a more efficient generation of oxygen by equalizing the pressure between the output lines of a sieve tank nearing fill completion and a sieve tank nearing the end of its purge cycle. U.S. Pat. Nos. 4,449,990 and 5,906,672, which are incorporated herein by reference, further describe the operation of pressure equalization valves. The oxygen that is being output by a particular sieve bed 300 may be stored in one or both product tanks 302. Both product tanks 302 are utilized in the embodiment of FIG. 5A.

As mentioned above, controller 506 can detect when the sieve tank 300 being pressurized has reached its adsorption capacity via pressure sensor 510. As shown in FIG. 5A, in one embodiment, pressure sensor 510 provides a signal indicative of pressure at the product tank side of a first check valve 516 that passes oxygen flow from the pressurized sieve tank 300 to interconnected product tanks 300 and a second check valve 516 that blocks oxygen flow from the interconnected product tanks 300 to the other sieve tank 300 while it is being regenerated. For example, the signal may reflect the difference between the pressurized oxygen gas and ambient air. In other embodiments, the pressure sensor 510 may be located anywhere in fluidic communication with the output of the sieve tank 300 being pressurized. Multiple pressure sensors 510 may be implemented if directly monitoring the output of each sieve tank 300 is desired. Once the pressurizing sieve tank 300 has reached its capacity, controller 506 shifts the pressurizing sieve tank 300 into a purging or exhausting cycle and shifts the other sieve tank 300, which is now regenerated, to a pressurizing cycle. This is the basic repetitive, alternating operation of the PSA process. For example, the controller 506 may shift or alternate cycles for sieve tanks 300 when the pressure sensor 510 detects 9.0 pounds per square inch gauge (psig), 12.5 psig, 16.5 psig, 19.0 psig, and 23.5 psig, with respect to the lowest to highest flow setting inputs 504. Of course, other psig values are envisioned and any suitable psig value may be implemented.

In one embodiment, bleed valve 502 has a variable "on delay" before activation to an open or "on" state. The variable "on delay" is associated, in one embodiment, with the flow setting input 504. For example, the controller 506 may activate the bleed valve 502 after an "on delay" of 3.3 seconds (sec), 3.2 sec, 3.0 sec, 2.9 sec, and 2.9 sec, with respect to the lowest to highest flow setting inputs 504. Of course, other "on delay" values are envisioned and any suitable "on delay" value may be implemented. In one embodiment, bleed valve 502 is de-activated by the controller 506 after the pressurizing sieve bed 300 has reached its capacity in conjunction with the end of the corresponding pressurizing cycle (i.e., the start of the next pressurization cycle for the other sieve tank 300). In general, bleed valve 502 "bleeds" oxygen out of one sieve tank 300 and into the other sieve tank 300 at a flow rate that is restricted by orifice 514. That is, oxygen is allowed to flow from the sieve tank 300 being pressurized to the sieve tank 300 being exhausted or purged. This oxygen flow assists the exhausting or purging of the sieve tank 300 to expel its captured nitrogen and to regenerate itself for its next pressurization cycle. Since the compressor 408 is variably pressurizing a sieve tank 300 based on the flow setting input 504, a bleed flow between the sieve tanks 300 that can be variably controlled can assist in the efficient purging of the exhausting sieve tank for the corresponding product gas output flow rate of the concentrator at a suitable purity level.

Generally, the higher the value of the flow setting input 504, the shorter the "on delay" time (i.e., closed time) and the longer the time that the bleed valve 502 will be open with more bleed flow being sent to the exhausting sieve tank 300. This is because higher pressurization levels may be used for the higher values for flow setting inputs 504. The higher pressurization levels may require more bleed flow to regenerate the exhausting or purging sieve tank 300. Conversely, the lower the value of the flow setting input 504, the longer the "on delay" time (i.e., closed time) and the shorter the time that the bleed valve 502 will be open. This is because lower pressurization levels may be used for the lower values for flow setting inputs 504. The lower pressurization levels may require less bleed flow to regenerate the exhausting or purging sieve tank 300. Accordingly, the variable "on delay" logic described above allows for an increased level of system efficiency in terms of maximizing the utilization of the oxygen that is generated by controlling the amount used in the purging of an exhausting sieve tank 300. In other embodiments, other variable logic may be used to vary other control parameters (e.g., bleed flow duration) for the bleed valve 502 for different flow setting inputs 504. In further embodiments, the variable logic may use other sensed parameters (e.g., pressure) to vary the "on delay" or other control parameters for different flow setting inputs 504.

As described above, the "on delay" time period prior to activation of the bleed valve 502 is dependant upon the value for the flow setting input 504 which in turn is based on certain other operating parameters, such as product tank output pressure, sieve tank output pressure, compressor speed, and volumetric capacity of various components. In one embodiment, the specific "on delay" time period for each flow setting input 504 may be determined empirically based on the physical specifications of the concentrator components. The "on delay" times for each value for the flow setting input 504 are then stored in a look-up table in the memory or logic of controller 506. Hence, after reading the flow setting input 504, controller 506 looks up the bleed valve variable "on delay" time from the look-up table stored in its memory or logic. The corresponding "on delay" time is then used to delay activation of the bleed valve 502 from the start of the pressurization cycle for the sieve tank 300 providing the bleed flow. As shown, the pressurization cycle starts after the pressure equalization valve PE closes (see timing diagram of FIG. 5B). Upon expiration of the "on delay" time, which can be monitored by a timer in the memory or logic, the bleed valve 502 is activated (i.e., opened or "on") and remains open until the start of the next PSA cycle in which the roles for the two sieve tanks 300 is shifted.

In other embodiments, the variable "on delay" may be based at least in part on a minimum "on delay" time. In another embodiment, the variable "on delay" may be based at least in part on one or more other parameters, such as product tank output pressure, sieve tank output pressure, compressor speed, and volumetric capacity of various components in any combination. In still other embodiments, the variable "on delay" may be based at least in part on a minimum "on delay" time in combination with one or more other parameters. For example, after the minimum "on delay" time, activation of the bleed valve 502 may be triggered if the other parameter exceeds a predetermined threshold at that time or any time before the current pressurization cycle is complete. Of course, alternate or opposite logic is envisioned and any suitable logical relation between the parameter and threshold may be implemented. In still other embodiments, activation of the bleed valve 502 may be triggered if the other parameter exceeds the predetermined threshold at any time during the pressurization cycle without a minimum "on delay."

In any of the embodiments described herein, bleed valve 502 may also have a variable "maximum on time" after activation in order to limit the continuous time it remains open or in the "on" state. The variable "maximum on time" may be associated with the flow setting input 504. For example, the controller 506 may de-activate the bleed valve 502 after a "maximum on time" of 2.2 sec, 2.4 sec, 2.6 sec, 2.8 sec, and 3.0 sec, with respect to the lowest to highest flow setting inputs 504. Of course, other "maximum on time" values are envisioned and any suitable "maximum on time" value may be implemented. In this embodiment, the bleed valve 502 would also be de-activated if the end of the current pressurization is reached before the "maximum on time" expires. Conversely, if the "maximum on time" expires before the end of the current pressurization cycle is reached, the bleed valve 502 could be activated again based on any combination of the "on delay" time or parameter triggers described above. If desired, the bleed valve 502 may also be fixed to provide a continuous bleed or fixed to a predetermined open time that is independent of the flow setting input 504. Additionally, the "on delay" time may be set to zero for a particular flow setting input 504 to provide a continuous bleed and the "maximum on time" may be set to zero for a particular flow setting input 504 to inhibit activation of the bleed valve 502.

FIG. 5B illustrates one embodiment of a timing diagram for the valves shown in FIG. 5A. As shown, after the first pressurization cycle, each pressurization cycle begins when the pressure equalization valve PE transitions from closed (i.e., off, de-activated) to open (i.e., on, activated). For example, upon the first activation of pressure equalization valve PV, pressurized oxygen from the first sieve tank 300 (i.e., associated with main valve MV1) flows through the pressure equalization valve PV to increase the pressure in the second sieve tank 300 (i.e., associated with main valve MV2). Exhaust valve EV2 is de-activated along with this activation of pressure equalization valve PE or shortly thereafter if the pressure equalization valve PE is to be used to assist in purging and regeneration of the second sieve tank 300. Shortly after this activation of the pressure equalization valve PE, main valve MV1 is de-activated and main valve MV2 is activated to switch inlet air flow generated by the compressor 408 from the first sieve tank 300 to the second sieve tank 300. The pressure equalization valve PE is de-activated shortly after the main valves MV1 and MV2 are switched. Typically, exhaust valve EV1 is activated along with this de-activation of pressure equalization valve PE to permit pressure equalization between the sieve tanks 300 to continue. However, if desired, the exhaust valve EV1 could be activated along with de-activation of main valve MV1 or shortly thereafter and before de-activation of pressure equalization valve PE. This process continues in alternating fashion to provide the PSA process.

In particular, it can be seen that the bleed valve 502 may be generally closed or "off" while the pressure equalization valve PE is open or "on," though this need not necessarily be the case. It can also be seen that the variable "on delay" time for the bleed valve begins when the pressure equalization valve PE transitions from closed or "off" to open or "on.," though this need not be the case as well. It may be beneficial under some circumstances to allow overlapping of the open or "on" states of these valves. In other words, under certain circumstances, both the bleed valve 502 and the pressure equalization PE may be utilized simultaneously or in any combination to provide bleed flow from the pressurizing sieve tank 300 to the other sieve tank 300 for its purging and regeneration.

FIG. 5C shows an exemplary path for bleed flow from sieve tank 1 through orifice 1 and sieve tank 2 to an exhaust gas outlet when main valve MV1, bleed valve 502, and exhaust valve EV2 are activated (i.e., open) and main valve MV2 and exhaust valve EV1 are de-activated (i.e., closed). FIG. 5D shows an exemplary alternate path for bleed flow from sieve tank 2 through orifice 1 and sieve tank 1 to the exhaust gas outlet when main valve MV2, bleed valve 502, and exhaust valve EV1 are activated and main valve MV1 and exhaust valve EV2 are de-activated. As shown by dotted lines, in one embodiment, the functions of bleed valve 502 and orifice 1 may be provided in a single component which may be referred to as a variable restrictor. In another embodiment, orifice 2 may provide a continuous fixed bleed flow in parallel to bleed valve 502 and orifice 1. Orifice 2 would establish a minimum bleed flow which could be increased by activation of the bleed valve 502 as described herein. In still another embodiment, a PE valve may be activated to provide or supplement bleed flow in combination with orifice 2 or the series combination of bleed valve 502 and orifice 1.

In another embodiment, the controller 506 may monitor the PSA shifting time (i.e., pressurization cycle time) to identify alternate modes of operation for certain Earth altitude ranges in which the concentrator is being operated. For example, a low altitude mode may be implemented for operation up to approximately 6,300 feet and a high altitude mode may be implemented for operation above 6,300 feet. Of course, other altitude ranges are envisioned and additional altitude modes may be implemented. PSA shifting time tends to increase at higher altitudes due to lower ambient atmospheric pressures (i.e., thinner air). Certain operating parameters of the concentrator may be adjusted based on a given altitude range in order to improve efficiency and sustain suitable levels of product gas volumetric output, flow rate, and purity.

Testing has demonstrated that a fixed "on delay" for bleed valve 502 based on flow setting input 504 may be acceptable in a low altitude mode of operation. However, the higher the altitude, the longer the shift time between pressurization of alternate sieve tanks 300 because the concentrator takes longer and longer to build up to the desired shift pressure. In response to the longer shift times, the concentrator may shift to a higher altitude mode which may adjust one or more operating parameters (i.e., product tank output pressure, sieve tank output pressure, bleed valve control) to keep the shift time in an optimum range. If a fixed "on delay" for the bleed valve 502 were maintained across a wide altitude range there may be little or no bleed flow at the lower elevations of the altitude range. Moreover, the fixed "on delay" could result in too much bleed flow at higher elevations when the shift time has been significantly stretched out. No bleed flow and too much bleed flow may result in the product gas from the concentrator being outside desired purity levels for operation at the lower and higher elevations of a wide altitude range.

Data was collected and analyzed at various altitudes over the range of 5,300 to 11,150 feet above sea level. Nominal values for low and high altitude shift times for each flow setting input 504 were identified. For example, 1) at the lowest flow setting input 504, nominal values of 5.5 and 14 seconds for low and high altitude shift times were identified and threshold of 6,300 feet was associated with transitioning from low altitude mode to high altitude mode; 2) at the next higher flow setting input 504, nominal values of 5 and 13 seconds for low and high altitude shift times were identified and a threshold of 6,200 feet was associated with transitioning from low altitude mode to high altitude mode; 3) at the middle flow setting input 504, nominal values of 5 and 11.5 seconds for low and high altitude shift times were identified and a threshold of 6,200 feet was associated with transitioning from low altitude mode to high altitude mode; 4) at the next higher flow setting input 504, nominal values of 5 and 10.5 seconds for low and high altitude shift times were identified and a threshold of 6,300 feet was associated with transitioning from low altitude mode to high altitude mode; and 5) at the highest flow setting input 504, nominal values of 5.5 and 11 seconds for low and high altitude shift times were identified and a threshold of 6,000 feet was associated with transitioning from low altitude mode to high altitude mode.

Suitable shift time thresholds may be established for transitioning from low altitude mode to high altitude mode (e.g., approximately 12 seconds) and for transitioning from high altitude mode to low altitude mode (e.g., approximately 5.5 seconds). Of course, different shift time thresholds can be established for different flow setting inputs 504. For example, the shift time thresholds for transitioning from low altitude mode to high altitude mode could range between 10.5 and 14 seconds for different flow setting inputs 504. Similarly, the shift time thresholds for transitioning from high altitude mode to low altitude mode could range between 5.0 and 5.5 seconds for different flow setting inputs 504. Typically, the thresholds will be different and the threshold for transitioning from high altitude mode to low altitude mode will be less than the other threshold to establish a suitable hysteresis. In another embodiment, transition between altitude modes can be delayed for a fixed time or until the shift times for a predetermined quantity of consecutive pressurization cycles (e.g., three consecutive cycles) indicate that the altitude mode transition is appropriate.

The bleed valve 502 may be controlled in any manner described herein for any altitude mode. Notably, the bleed valve 502 may be controlled differently in different altitude modes. Accordingly, preferred bleed valve control techniques can be implemented based at least in part on altitude mode and transitions in altitude modes can produce corresponding transitions in bleed valve control techniques.

In one embodiment, an "on delay" time associated with activation the bleed valve 502 and the PSA shifting time (i.e., pressurization cycle time) may have a generally linear relation encompassing the range of the flow setting inputs 506. The shift time may be represented by the shift pressure set-point for each flow setting input 506 because the shift time is the time it takes a given sieve tank 300 to reach a pressure related to its full capacity. In the embodiment being described, pressure build in the sieve tank 300 may be assumed to be linear. This allows a bleed valve activation pressure to be expressed as a ratio of pressure set-point for each flow setting input 506. The ratio may then be used to determine a threshold pressure value. During the pressure build up, if the pressure exceeds the threshold pressure value, the controller 506 activates (i.e., opens) the bleed valve 502. This may ensure there is at least enough bleed flow to maintain a desired level of purity while also limiting bleed flow to avoid unnecessary loss of oxygen. In other embodiments, the "on delay" time may be a non-linear function of the PSA shifting time. Similarly, the function used to determine the "on delay" time may be different for different flow setting inputs 506 in other embodiments.

The table below shows exemplary pressure set-points for each flow setting input 506 when the concentrator is operating in a low altitude mode (LAM). In one embodiment, pressure set-points for high altitude mode (HAM) can be determined from the exemplary pressure set-points for LAM using the following equation:

$$\text{HAM Pressure Set-Point} = \text{LAM Pressure Set-Point} * \text{Ratio} \quad (1),$$

where the Ratio may be 0.875 for all flow setting inputs 506. Of course, HAM pressure set-points can be established using other techniques or other suitable criteria. For example, the Ratio may be a different value or may be replaced by a variable function for any particular flow setting input 506. Additionally, where additional altitude modes are implemented any suitable technique or criteria may be used to establish alternate pressure set points for each altitude mode.

In one embodiment, the threshold values for triggering activation of the bleed valve 502 during HAM may be determined using the following equation:

$$\text{HAM Pressure Threshold} = \text{HAM Pressure Set-Point} * \text{Ratio} \quad (2),$$

where the Ratio may be: i) 0.55 for the lowest flow setting input 506, ii) 0.60 for the next higher flow setting input 506, iii) 0.65 for the middle flow setting input 506, iv) 0.70 for the next higher flow setting input 506, and v) 0.75 for the highest flow setting input 506. In another embodiment, the Ratio may be 0.90 for all flow setting inputs 506. Of course, HAM pressure thresholds can be established using other techniques or other suitable criteria. For example, the constant may be a different value or may be replaced by a variable function for any particular flow setting input 506. Additionally, where additional altitude modes are implemented any suitable technique or criteria may be used to establish alternate pressure thresholds for each altitude mode.

Example 1

| Flow Setting | LAM Pressure Set-Point (psig) | HAM Pressure Set-Point (psig) | Ratio | HAM Pressure Threshold for Bleed Valve Activation (psig) |
|---|---|---|---|---|
| 1 | 9.0  | 7.88  | .55 | 4.33 |
| 2 | 12.5 | 10.94 | .60 | 6.56 |
| 3 | 16.5 | 14.44 | .65 | 9.38 |
| 4 | 19.0 | 16.63 | .70 | 11.64 |
| 5 | 23.5 | 20.56 | .75 | 15.42 |

Example 2

| Flow Setting | LAM Pressure Set-Point (psig) | HAM Pressure Set-Point (psig) | Ratio | HAM Pressure Threshold for Bleed Valve Activation (psig) |
|---|---|---|---|---|
| 1 | 9.0  | 7.88  | .90 | 7.09 |
| 2 | 12.5 | 10.94 | .90 | 9.84 |
| 3 | 16.5 | 14.44 | .90 | 12.99 |
| 4 | 19.0 | 16.63 | .90 | 14.96 |
| 5 | 23.5 | 20.56 | .90 | 18.51 |

In another embodiment, the controller 506 may utilize a timer function to monitor PSA cycle shift time. This monitored shift time measurement may be compared against shift time ranges stored in non-volatile memory. The controller 506 may use the result of this comparison to determine if the concentrator should be operating in low or high altitude modes. In low altitude mode, for each flow setting input 504, the concentrator may operate from a fixed pressure value that is stored in non-volatile memory. In high altitude mode, the concentrator may operate from a fixed pressure value for each flow setting input 504 that is based at least in part on the corresponding low altitude fixed pressure value.

In yet another embodiment, in low altitude mode, for each flow setting input 504, the concentrator may operate from a fixed "on delay" time for activation of the bleed valve 502 that is stored in non-volatile memory. In high altitude mode, the concentrator may operate from a variable bleed valve activation time that is scaled based on the fixed pressure value for each flow setting input 504 or the monitored PSA cycle shift time. The bleed valve scale factor may be calculated from the fixed pressure value or the monitored PSA cycle shift time.

The aforementioned functions can be performed either as software or controller logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desire manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or another type of executable instructions. It will be appreciated by one of ordinary skill in the art that the form of software is dependent on, for example, requirements of a desired application, the environment it runs on, and/or the desires of a designer/programmer or the like.

The systems and methods of the present invention can be implemented on a variety of platforms including, for example, networked control systems and stand-alone control systems. Additionally, the logic, databases or tables shown and described herein preferably reside in or on a computer readable medium such as, for example, a Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, and optically readable mediums including CD-ROM and DVD-ROM. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

FIGS. 5E and 5F further illustrate an exemplary embodiment of a valve assembly 214 that includes bleed valve 502 and other components. In this embodiment, bleed valve 502, pressure equalization valve PE a conserver valve 512, fixed orifice 514, fixed orifice 515, and check valves 516 are mounted or affixed to a block-like manifold body having a plurality of inlets, outlets and inner passageways connecting the inlets, outlets and valves as shown. So configured, the valve assembly 214 results in a space and weight savings that is adaptable to a portable oxygen concentrator and other devices. The configuration also allows for easy service and replacement of the valve assembly 214 should that be necessary. In other embodiments, the concentrator may include discrete components or any suitable combination of components in one or more valve assemblies. In particular, bleed valve 502 and fixed orifice 514 may be combined in a modular assembly.

Output Port

In one embodiment of the present invention, output port 108 includes a suitable air filter. Though the oxygen exiting the sieve and product tanks has already been filtered prior to the nitrogen-oxygen separation process, additional filtering may be of assistance to some patients. Referring now to FIG. 6A, the perspective view of one embodiment of output port 108 is shown. The output port 108 includes a main body 600, input 602, extension 604 and output 610. Input 602 is configured to meet with pneumatic tubing that delivers oxygen. The oxygen received through input 602 enters main body 600. Main body 600 includes a suitable filter therein such as, for example, a HEPA filter or other suitable filter, for the filtering the oxygen. Extension 604 includes a key surface 606 and threads 608. The surface 606 facilitates a proper orientation of the output port 108 during our assembly with the housing of the oxygen concentrator. Threads 608 facilitate fastening of the output port 108 to the housing of the oxygen concentrator via a HEX nut or other type of fastener. Output 610 is configured to mate with tubing that delivers the oxygen to the patient or a medical accessory.

Figure 6B:
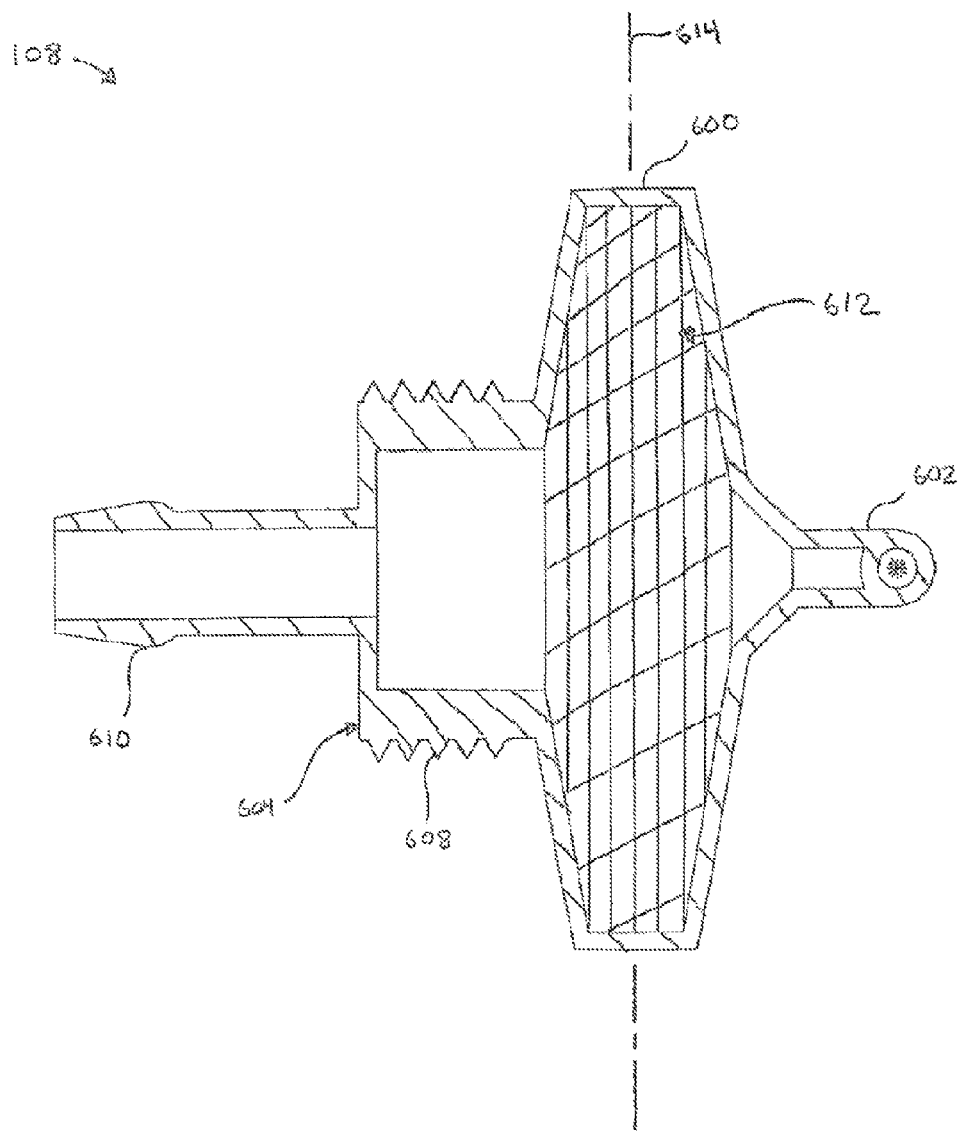

Referring now to FIG. 6B, a day cross-sectional view taken along a section lines 6B-6B of FIG. 6A is shown. The filter of main body 600 is shown at 612. Filter 612 occupies a substantial portion of the inner space of main body 600 to filter the oxygen being received through input 602. As such, filter 612 has a shape and geometry that complements the shape and geometry of the inner space of main body 600. In one embodiment, filter 612 is made of a Boro-Silicate Glass microfiber and is hydrophobic. Filter 612 also provides for a filtration efficiency of greater than 99.99% for particle sizes 0.2 micrometers or greater. Other filters having less than all of these properties may be used as well.

In one embodiment, the main body 600 is made from a polypropylene material and its inner space provides for an effective filtration area of 3.5 cm². The main body material can be any suitable material and the filtration area can be made larger or smaller than described. In one embodiment, output port 108 is preferably fabricated by joining two sections that interface in the region of the main body 600 to form the entire output port 108. In this example, two sections are shown being divided by interface axis 614 extending through main body 600. Filter 612 is inserted into one of the sections forming part of the inner space of main body 600. The other section would then be joined through bonding or welding, thereby sealing filter 612 into the inner space of main body 600. In other embodiments, the two sections can be joined via mating threads or other non-permanent connections that would allow removal and replacement of filter 612.

Pressure Sensor Calibration and Conserver

FIG. 7 illustrates one embodiment of a process 700 for calibrating pressure sensor 510 within controller 506. The rectangular elements denote "processing blocks" and represent computer software instructions or groups of instructions. The diamond shaped elements denote "decision blocks" and represent computer software instructions or groups of instructions which affect the execution of the computer software instructions represented by the processing blocks. Alternatively, the processing and decision blocks represent steps performed by functionally equivalent circuits such as a digital signal processor circuit or an application-specific integrated circuit (ASIC). The flow diagram does not depict syntax of any particular programming language. Rather, the flow diagram illustrates the functional information one skilled in the art may use to fabricate circuits or to generate computer software to perform the processing of the system. It should be noted that many routine program elements, such as initialization of loops and variables and the use of temporary variables are not shown. Also the order flow may be changed with the same results being obtained.

The calibration routine, for example, may be performed by a qualified technician using an adjustable external pressure source. Of course, other scenarios are possible and any procedure that suitably accomplishes the pressure sensor calibration may be implemented. In block 702, a signal (e.g., analog to digital count (A-D count)) from the pressure sensor 510 is read by the controller 506 after an external pressure source is adjusted to a first fixed pressure setting and pressure is applied to the pressure sensor. For example, the first fixed pressure setting may be a pressure associated with normal operation of the concentrator, such as 10 psig. For example, controller 506 includes as one of its structures an analog-to-digital converter that allows it to read analog signals that emanate from sensors such as pressure and flow sensors. The conversion of an analog sensor signal to a digital or binary value allows the controller to read and use the sensor signal in its processing. In other embodiments, the first fixed pressure setting can be any pressure setting including ambient or vacuum. In block 704, a value for the signal read in 702 (e.g., corresponding A-D count) is stored in memory.

In block 706, the signal (e.g., A-D count) from the pressure sensor 510 is read by the controller 506 after the external pressure source is adjusted to a second fixed pressure setting. For example, the second fixed pressure setting may also be a pressure associated with normal operation of the concentrator, such as 20 psig. Similar to the first pressure setting, the second pressure setting can be any pressure setting. Block 708 stores a value for the signal read in 706 (e.g., corresponding A-D count) in memory. Block 710 generates a linear extrapolation (Y=m(X)+B) using the first and second signal values (e.g., A-D count readings). The linear extrapolation is then used in block 712 by controller 506 to convert signal values (e.g., A-D counts) from the pressure sensor 510 to psig. In the linear extrapolation, X represents signal values (e.g., pressure sensor A-D counts or readings) and Y represents pressure in psig. In alternate embodiments, any pressure setting can be used from unitless or un-calibrated measures of pressure to external calibrated pressure sources.

FIG. 8 illustrates one embodiment of a conserver process 800 for determining a time duration associated with providing a bolus of gas, such as oxygen, to a user of the oxygen concentrator 100. "Bolus," as used herein includes, but is not limited to, a dose or pulse of concentrated product gas, such as oxygen, provided to the user via a suitable user interface, such as a nasal cannula or nasal mask. Bolus parameters relating to flow through pneumatic components include duration and amplitude. The duration parameter relates to activating and de-activating a valve to start and end the bolus. The amplitude parameter relates to flow capacity of the components and pressure of the product gas. Oxygen concentrator 100 can include, for example, a conserving device for controlling the flow of oxygen to the patient. For example, the conserving device may be adjustable in relation to one or more parameters to conserve power consumption of the oxygen concentrator 100 while maintaining suitable purity, flow rate, and volume of the product gas. In one embodiment, the conserving device is formed by controller 506, flow sensor 508, pressure sensor 510 conserver valve 512, and fixed orifice 515 (see, FIG. 5A). The conserver process 800 represents one embodiment of logic that can reside within controller 506. Controller 506 uses, for example, flow sensor 508 to monitor the breathing of a user to determine breathing characteristics (e.g., breath rate, inhalation, exhalation, volume, flow, etc.) of the user. Upon the start of inhalation (i.e., the end of exhalation), controller 506 is programmed to deliver a bolus of gas, such as oxygen, to the user. In this regard, the size of the bolus can be fixed or determined at least in part from the patient's breathing characteristics (e.g., breathing rate, duration of inhalation, volume, flow, etc.). Once fixed or determined, controller 506 controls the on and off state of conserver valve 512 to deliver the proper bolus of gas to the patient. For example, a bolus can be provided during the inhalation portion of each breathing cycle.

In block 802, the controller 506 has detected a trigger associated with the patient's breathing characteristics, determined that a bolus of gas is to be delivered to the patient, and opened or switched the conserver valve 512 to dispense concentrated product gas to the patient. A loop now begins where the controller 506 reads the signal (e.g., A-D count) of the pressure sensor (block 802), converts the signal (e.g., A-D count) to psig (block 804), and sums the psig values until a pre-determined psig value is reached (block 806). For example, the pre-determined summation of psig values may relate to a pre-determined volumetric measure of concentrated breathing gas to be provided by the bolus. The pre-determined volumetric measure of concentrated breathing gas may be based at least in part on the patient's breath rate and a desired output volume over a pre-determined time duration (e.g., 300 cc/min). For example, the physical characteristics of the fixed orifice 515, the monitored pressure of the product tanks 302, and the time the conserver valve 512 is activated to provide product gas flow may be considered by the controller 506 in order to provide the desired volume of product gas in a given bolus. The relation of pressure over time for product gas flow through a fixed orifice is a classic integral calculus function. Where the pressure is variable, the time the conserver valve 512 is activated is adjustable in order to provide the desired volume of product gas. Accordingly, the controller 506 may control the conserver valve 512 based at least in part on the monitored pressure.

In block 804, the conversion from signal value (e.g., pressure sensor A-D count) to psig is accomplished using the linear extrapolation obtained from FIG. 7. In other embodiments, alternative methods of obtaining the psig values from the signal value (e.g., A-D counts) can also be utilized. In block 806, the psig values are summed by adding them together such as, for example, by the formula P=P+PSIG. In the formula, PSIG represents the current psig reading and P represents the current summation of pressures. This formula is derived from the classic integral calculus function defining the relation of pressure over time for product gas flow through a fixed orifice discussed above. In an alternative embodiment, the signal values (e.g., A-D counts) from the pressure sensor 510 can be summed until a pre-determined summation value (e.g., summation A-D count) is reached. Once the summation of pressures equals a pre-determined pressure summation threshold, at 810, the controller 506 closes the conserver valve 512 and waits for the next bolus trigger to occur. For example, the pre-determined pressure summation threshold may relate to a pre-determined volumetric measure of concentrated breathing gas to be provided by the bolus.

The pre-determined volumetric measure of concentrated breathing gas may be based at least in part on the patient's breath rate and a desired output volume over a pre-determined time duration (e.g., 840 cc/min). For example, the desired output flow rate setting (e.g., 840 cc/min) may be divided by the patient's breath rate to allocate the corresponding desired volume for the longer time scale to individual boluses for each patient breath. For an exemplary breath rate of 20 bpm, the desired volume for each bolus may be 42 cc. Similarly, for an exemplary breath rate of 10 bpm, the desired volume for each bolus may be 84 cc. Normally, a bolus would be delivered with each patient breath. However, the concentrator may intentionally skip a breath under certain circumstances to ensure that suitable product gas purity levels and system efficiency is achieved. For example, if the breath rate exceeds a predetermined rate (e.g., 36 bpm), the concentrator may not provide a bolus with every breath and may selectively skip breaths in a manner the achieves suitable product gas purity levels and system efficiency.

FIG. 9 illustrates one embodiment of timing operation of the conserver valve 512 with respect to a breathing characteristic (e.g., inhalation) associated with a user breathing cycle (i.e., BREATH 900). An exemplary breathing cycle 901 is shown with an inhalation period followed by an exhalation period. Flow sensor 508 measures a flow rate associated with the user breathing cycle when the conserver valve 512 is diverting user breathing through the vent port, which is represented by FLOW 902 and an exemplary flow signal 903 corresponding to the exemplary breathing cycle 901. Flow signal 903, for example, can represent analog signal levels, digital representations of analog signal levels, or actual flow rate units. In any event, trigger threshold 904 is established for flow signal 903. Trigger threshold 904 can, depending on the particular implementation, be a zero-crossing point, offset (positive or negative) from the zero-crossing point, an average flow per cycle, or off-set (positive or negative) from the average flow. In the embodiment shown in FIG. 9, the trigger threshold 904 is shown as occurring just after the inhalation phase has started. This is an example of a positive offset from the zero-crossing point. In one embodiment, the trigger threshold can be 12 standard cubic centimeters per minute (sccm).

Once the trigger threshold 904 has been reached by flow signal 903, controller 506 opens conserver valve 512 for a time duration long enough to deliver the required size bolus 905 to the user. In one embodiment, the time duration that the conserver valve 512 remains open may be determined by the logic of process 800 (FIG. 8). As described above in reference to FIG. 8, once the summation of pressures reaches the pre-determined summation value, conserver valve 512 is closed 906 by controller 506. The controller 506 may ignore or otherwise avoid taking action in relation to the trigger threshold 904 at least until a time duration associated with breath rates is exceeded in order to avoid triggering another bolus 905 before the start of the next inhalation. This may be referred to as a trigger lock-out period 907. The trigger lock-out period 907 can be determined as a percentage of a breathing characteristic (e.g., breath rate, breath cycle, exhalation, or other breathing characteristics including flow, flow rate and pressure) for an average person, exemplary person, or a particular person, such as the patient. For example, if a breath rate of 350 milliseconds (msec) is selected, the trigger lock-out period would be some percentage of 350 msec, such as 175 msec. This trigger lock-out period 907 ensures that the next trigger is not falsely or prematurely initiated until the start of the patient's next inhalation. After expiration of the trigger lock-out period 907, the next trigger threshold is active. In one embodiment, after the trigger lockout period, the controller 506 may also wait for the flow signal to fall below the trigger threshold 904 before enabling the next activation of the conserver valve 512. In this manner, a bolus 905 of gas (e.g., oxygen) may be delivered to the patient each time flow signal 903 rises through the trigger threshold 904 after the start of an inhalation portion of a breathing cycle. As described above, the concentrator may intentionally skip a breath under certain circumstances to ensure that suitable product gas purity levels and system efficiency is achieved.

The conserver valve 512 may also be controlled in any manner described herein for any altitude mode. Notably, the conserver valve 512 may be controlled differently in different altitude modes. Accordingly, preferred conserver valve control techniques can be implemented based at least in part on altitude mode and transitions in altitude modes can produce corresponding transitions in conserver valve control techniques.

In one embodiment, in high altitude mode, the controller 506 may automatically adjust operation of the conserver valve 512 to maintain suitable levels of purity, flow rate, and volume for the product gas as elevation changes. If not adjusted, for example, the conserver valve 512 may stay activated longer as the PSA cycle shift time increases in relation to higher elevations. This may result in larger bolus volumes than necessary and higher product gas outputs than desired. For example, in low altitude mode, the concentrator may operate using a low altitude fixed time duration for activation of the conserver valve 512 for a given flow setting input 504. The low altitude fixed time duration may be different for different flow setting inputs 504. Each low altitude fixed time duration may be a function of PSA cycle shift time and decay in pressure of the concentrated product gas associated with the shifting. These low altitude fixed time durations may be stored in non-volatile memory.

Similarly, in high altitude mode, the concentrator may operate using a high altitude fixed time duration for activation of the conserver valve 512 at a given flow setting input 504. The high altitude fixed time duration may be different for different flow setting inputs 504. Each high altitude fixed time duration may be a function of the low altitude fixed time duration for the corresponding flow setting input 504. The functional relationship between the low and high altitude fixed time durations may be different for different flow setting inputs 504. In other words, the algorithm defining the function at a given flow setting input 504 may be different from the algorithm defining the function at a different flow setting input 504. These high altitude fixed time durations may be stored in non-volatile memory. In other embodiments, values for certain parameters of the functions (i.e., algorithms), particularly parameters that vary for different flow setting inputs 504, may be stored in non-volatile memory.

With reference to FIG. 10, another exemplary embodiment of a product gas concentrator 10 may include an input device 12, a product gas source 14, a pressure sensor 16, a conserver valve 18, and a controller 20. The input device 12 may be used to select a first desired output flow rate setting for the concentrated product gas. The product gas source 14 may provide the concentrated product gas for dispensing. The pressure sensor 16 may monitor a pressure of the concentrated product gas. The conserver valve 18 may include an output connection, a vent connection, and a gas connection. The output connection may be associated with a user 22. The vent connection may be associated with a vent port 24. The gas connection may be associated with the concentrated product gas. The output connection may be switched from the vent connection to the gas connection and vice versa. The controller is in operative communication with the input device 12 and pressure sensor 16 and may selectively switch the conserver valve 18 to selectively dispense the concentrated product gas based at least in part on the selected output flow rate setting and monitored pressure. For example, the pressure sensor 16 may monitor pressure between the conserver valve 18 and the product gas source 14. In another embodiment, the pressure sensor 16 may monitor pressure in another suitable location.

In one embodiment, the controller 20 may store a first pressure value based at least in part on the corresponding monitored pressure. The controller 20 may also store a second pressure value based at least in part on the corresponding monitored pressure after the input device 12 is used to select a second desired output flow rate setting. In this embodiment, the controller 20 may determine an intermediate pressure value between the first and second pressure values based at least in part on a linear relation between the first and second pressure values and the monitored pressure.

In another embodiment, the product gas concentrator 10 may also include a flow sensor 26. The flow sensor 26 may monitor a flow indicative of a breathing cycle for the user 22. The controller 20 may be in operative communication with the flow sensor 26. For example, the flow sensor 26 may monitor flow between the conserver valve 18 and the vent port 24. In the embodiment being described, the controller 20 may determine a breathing characteristic of the user 22 based at least in part on the monitored flow. The controller 20 may selectively switch the conserver valve 18 based at least in part on the determined breathing characteristic. In another embodiment, the flow sensor 26 may monitor a flow indicative of a breathing cycle for the user 22 in another suitable location.

In the embodiment being described, the controller 20 may determine a start time for dispensing a bolus of concentrated product gas to the user 22 via the conserver valve 18 based at least in part on a relation between the determined breathing characteristic and a trigger threshold indicative of inhalation. The controller 20 may determine a pressure summation threshold based at least in part on the selected output flow rate setting. In the embodiment being described, the controller 20 may also determine the start time for dispensing the bolus of concentrated product gas based at least in part on expiration of a lock-out time associated with a previous bolus. The controller 20 may determine a time duration for dispensing the bolus of concentrated product gas based at least in part on a relation between the monitored pressure and the pressure summation threshold.

With reference to FIG. 11, an exemplary embodiment of a process 50 for providing a concentrated product gas may begin at 52, where a first desired output flow rate setting for the concentrated product gas may be selected. Next, a product gas source for dispensing the concentrated product gas may be provided (54). At 56, a pressure of the concentrated product gas may be monitored. Next, an output connection associated with a user may be selectively switched from a vent connection associated with a vent port to a gas connection associated with the concentrated product gas and vice versa to selectively dispense the concentrated product gas based at least in part on the selected output flow rate setting and monitored pressure (58).

In one embodiment, the process 50 may also include storing a first pressure value based at least in part on the monitored pressure, selecting a second desired output flow rate setting for the concentrated product gas, storing a second pressure value based at least in part on the monitored pressure, and determining an intermediate pressure value between the first and second pressure values based at least in part on a linear relation between the first and second pressure values.

In still another embodiment, the process 50 may also include monitoring a flow indicative of a breathing cycle for the user and determining a breathing characteristic of the user based at least in part on the monitored flow. In this embodiment, the selective switching in 58 may be based at least in part on the monitored breathing characteristic. In the embodiment being described, the process 50 may further include determining a start time for dispensing a bolus of concentrated product gas to the user via the output connection based at least in part on a relation between the monitored breathing characteristic and a trigger threshold indicative of inhalation. The process 50 may also include determining the start time for dispensing the bolus of concentrated product gas based at least in part on expiration of a lock-out time associated with a previous bolus. Additionally, in this embodiment, the process 50 may also include determining a pressure summation threshold based at least in part on the selected output flow rate setting and determining a time duration for dispensing the bolus of concentrated product gas based at least in part on a relation between the monitored pressure and the pressure summation threshold.

While the present invention has been illustrated by the description of embodiments thereof, and while the embodiments have been described in considerable detail, it is not the intention of the specification to restrict or in any way limit the scope of the appended claims to such detail. Additional advantages and modifications will readily appear to those skilled in the art. For example, components that are described as being connected, affixed, or joined, can be connected, affixed or joined directly or indirectly such as through one or more intermediary components. Furthermore, sizes and geometries of various components can be changed from the various embodiments and examples shown and described herein. Therefore, the invention, in its broader aspects, is not limited to the specific details, the representative apparatus, and illustrative examples shown and described. Accordingly, departures may be made from such details without departing from the spirit or scope of the applicant's general inventive concept.

The invention claimed is:

1. A method of providing a concentrated product gas, comprising:
   selecting a first desired output setting for the concentrated product gas;
   providing a product gas source for supplying the concentrated product gas to be dispensed;
   monitoring a pressure of the concentrated product gas; and
   selectively switching an output connection associated with a user from a vent connection associated with a vent port to a gas connection associated with the concentrated product gas and vice versa to selectively dispense a bolus of concentrated product gas based at least in part on the selected output setting and monitored pressure;
   wherein selectively switching comprises comparing a pressure summation to a pressure summation threshold associated with the bolus.

2. The method of claim 1, further comprising:
   determining the pressure summation threshold based at least in part on the selected output setting; and
   determining a time duration for dispensing the bolus of concentrated product gas based at least in part on a relation between the monitored pressure and the pressure summation threshold.

3. The method of claim 1, further comprising:
   monitoring a flow indicative of a breathing cycle for the user; and
   determining a breathing characteristic of the user based at least in part on the monitored flow; and
   wherein the selective switching is based at least in part on the monitored breathing characteristic.

4. The method of claim 3, further comprising:
   determining the start time for dispensing the bolus of concentrated product gas based at least in part on expiration of a lock-out time associated with a previous bolus.

5. The method of claim 3, further comprising:
   determining a start time for dispensing the bolus of concentrated product gas to the user via the output connection based at least in part on a relation between the determined breathing characteristic and a trigger threshold indicative of inhalation.

6. The method of claim 3, further comprising:
   determining the pressure summation threshold based at least in part on the selected output setting; and
   determining a time duration for dispensing the bolus of concentrated product gas based at least in part on a relation between the monitored pressure and the pressure summation threshold.

7. The method of claim 6, further comprising:
   determining the pressure summation threshold based at least in part on the determined breathing characteristic.

8. The method of claim 6, further comprising:
   determining the pressure summation threshold based at least in part on a user breath rate.

9. The method of claim 3, wherein the selective switching skips dispensing the concentrated product gas during selected breaths based at least in part on the determined breathing characteristic.

10. The method of claim 1, wherein the pressure summation is a summation of PSIG readings.

11. The method of claim 1, wherein the selective switching to selectively dispense the concentrated product gas maintains an acceptable purity level for the concentrated product gas over a plurality of predetermined altitude ranges.

* * * * *